United States Patent
Roberts et al.

(10) Patent No.: US 7,202,223 B2
(45) Date of Patent: *Apr. 10, 2007

(54) NUCLEOSIDE COMPOUNDS FOR TREATING VIRAL INFECTIONS

(75) Inventors: Christopher D. Roberts, Belmont, CA (US); Jesse D. Keicher, Menlo Park, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 10/861,090

(22) Filed: Jun. 4, 2004

(65) Prior Publication Data

US 2006/0079468 A1   Apr. 13, 2006

Related U.S. Application Data

(60) Provisional application No. 60/515,153, filed on Oct. 27, 2003.

(51) Int. Cl.
*A61K 31/70* (2006.01)
*C07H 19/14* (2006.01)

(52) U.S. Cl. .......... 514/43; 536/26.23; 536/26.26; 536/26.7; 536/27.2

(58) Field of Classification Search .......... 514/43; 536/26.23, 26.26, 26.7, 27.2
See application file for complete search history.

(56) References Cited

U.S. PATENT DOCUMENTS

| | | | |
|---|---|---|---|
| 4,140,851 A | 2/1979 | Townsend et al. | |
| 4,892,865 A | 1/1990 | Townsend et al. | |
| 4,927,830 A | 5/1990 | Townsend et al. | |
| 4,968,686 A | 11/1990 | Townsend et al. | |
| 5,681,941 A | 10/1997 | Cook et al. | |
| 5,763,597 A | 6/1998 | Ugarkar et al. | 536/27.13 |
| 5,798,340 A | 8/1998 | Bischofberger et al. | |
| 5,811,534 A | 9/1998 | Cook et al. | 536/23.1 |
| 5,824,796 A | 10/1998 | Petrie et al. | |
| 5,844,106 A | 12/1998 | Seela et al. | |
| 6,004,939 A | 12/1999 | Chen et al. | |
| 6,054,442 A | 4/2000 | Chen et al. | |
| 6,150,510 A | 11/2000 | Seela et al. | |
| 6,211,158 B1 | 4/2001 | Seela et al. | 514/44 |
| 6,479,651 B1 | 11/2002 | Seela et al. | 536/22.1 |
| 6,593,306 B1 | 7/2003 | Chen et al. | |
| 6,777,395 B2 | 8/2004 | Blat et al. | 514/43 |
| 7,094,768 B2 * | 8/2006 | Roberts et al. | 514/45 |
| 2002/0035077 A1 | 3/2002 | Tam et al. | |
| 2003/0096981 A1 | 5/2003 | Seela et al. | |
| 2003/0153744 A1 | 8/2003 | Mekouar et al. | |
| 2004/0014108 A1 | 1/2004 | Eldrup et al. | |
| 2004/0014957 A1 | 1/2004 | Eldrup et al. | |
| 2004/0067901 A1 | 4/2004 | Bhat et al. | |
| 2004/0072788 A1 | 4/2004 | Bhat et al. | |

FOREIGN PATENT DOCUMENTS

| | | |
|---|---|---|
| JP | 61-229897 | 10/1986 |
| WO | WO/1991/10671 | 7/1991 |
| WO | WO/1994/18215 | 8/1994 |
| WO | WO/1994/24144 | 10/1994 |
| WO | WO/1995/07919 | 3/1995 |
| WO | WO/1997/49833 | 12/1997 |
| WO | WO/2001/90121 | 5/2001 |
| WO | WO/2001/72764 | 10/2001 |
| WO | WO/2002/18404 | 3/2002 |
| WO | WO/2002/057287 | 7/2002 |
| WO | WO/2002/057425 | 7/2002 |
| WO | WO 03/051899 | 6/2003 |
| WO | WO 03/055896 | 7/2003 |
| WO | WO/2003/061576 | 7/2003 |
| WO | WO/2003/068244 | 8/2003 |
| WO | WO/2004/007512 | 1/2004 |
| WO | WO 04/011478 | 2/2004 |
| WO | WO 04/028481 | 4/2004 |
| WO | WO/2004/043977 | 5/2004 |

OTHER PUBLICATIONS

Bergstrom, D. et al. "Antiviral Activity of C-5 Substituted Tubercidin Analogues," *J. Med. Chem.* 1984, 27, 285-292.

Hobbs, F.W., Palladium-Catalyzed Synthesis of Alkynylamino Nucleosides. A Universal Liner for Nucleic Acids, *J. Org. Chem.*, 1989, 54:3420-22.

(Continued)

*Primary Examiner*—L. E. Crane
(74) *Attorney, Agent, or Firm*—Foley & Lardner LLP; Junrui Yang

(57) ABSTRACT

Disclosed are compounds, compositions and methods for treating viral infections caused by a flaviviridae family virus, such as hepatitis C virus. Such compounds are represented by Formula I as follows:

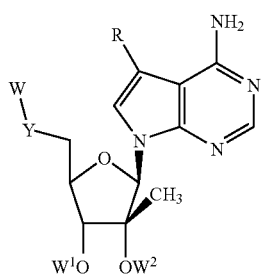

wherein, each of R, Y, W, $W^1$ and $W^2$ are as defined herein.

24 Claims, No Drawings

OTHER PUBLICATIONS

DeClercq, E., et al., Nucleic Acid Related Compounds. 51. Synthesis and Biological Properties of Sugar-Modified Analogues of the Nucleoside Antibiotices Tubercidin, Toyocamycin, Sangivamycin, and Formycin, *J. Med. Chem.*, 1987, 30:481-486.

Bzowska, et al., "7-Deazapurine 2'-deoxyribofuranosides are noncleavable competitive inhibitors of *Escherichia coli* purine nucleoside phosphorylase (PNP)," *Acta Biochimica Polonica*, 45(3);755-768 (1998).

Seela et al., "Pyrrolo[2,3d]Pyrididine Nucleosides: 7-Deaza-2'-Deoxyadenosines," *Nucleosides, Nucleotides & Nucleic Acids*, 19(1 &2):237-251 (2000).

Migliaccio et al., "Characterization of Resistance to Non-obligate Chain-terminating Ribonucleoside Analogs That Inhibit Hepatitis C Virus Replication *in Vitro*" *J.Biol.Chem.* 278(49):49164-49170 (2003).

Carroll et al., "Inhibition of Hepatitis C Virus RNA Replication by 2'-Modified Nucleoside Analogs" *J.Biol.Chem* 278(14):11979-11981 (2003).

Seela et al, "Oligonucleoties containing 7-deazaadenines: the influence of the 7-substituent chain length and charge on the duplex stability," *Helvetica Cimica Acta.*, 82(11):1878-1898 (1999).

Rosemeyer, et al., "Stereoelectronic effects of modified purine bases on the sugar conformation of nucleosides: pyrrolo[2,3-d] pyrimidines," *Journal of the Chemical Society, Perkin Transactions 2: Physical Organic Chemistry*, 11:2341-2346 (1997).

Rosemeyer, et al., "Steric and stereoelectronic effects of 7-deazapurine bases on the sugar conformation of 2'-deoxynucleosides" *Nucleosides & Nucleotides* 16(7-9) 1447-1451 (1997).

Rosemeyer, et al., "Stereoelectronic effects of modified purines on the sugar conformation of nucleosides and fluorescence properties," *Nucleosides & Nucleotides*, 16(5&6):821-828 (1997).

Seela, et al., "Palladium-catalyzed cross coupling of 7-iodo-2'-deoxytubercidin with terminal alkynes" *Synthesis* 6:726-730 (1996).

Schneller, et al., "Biological Activity and a modified synthesis of 8-Amino-3-β-D-ribofuranosyl-1,2,4-triazolo[4,3-a]pyrazine, and isomer of formycin," *J. Med Chem.* 27, 924-928 (1984).

Giziewicz, et al., "Antiviral and antimetabolic activities of formycin and its N-, N2-, 2'-O- and 3'-O-methylated derivatives," *Biochemical Pharmacology* 24, 1813-1817, (1975).

Bergstrom, et al., Pyrrolo[2,3-d]pyrimidine Nucleoside Antibiotic Analogues. Synthesis via Organopalladium Intermediates Derived from 5-Mercuritubercidin, *J. Org Chem.* 46:1423-1431 (1981).

Sharma, et al., "Synthesis of 5'-Substituted Derivatives of the Pyrrolo [2,3-d]-Pyrimidine Nucleoside Sangivamycin and their Effect on Protein Kinase A and C Activity," *Nucleosides & Nucleotides* 12(3&4) 295-304 (1993).

Müller, et al., "Deaza-2-phenyladenines: Structure-Activity Relationship of Potent A1 Selective Adenosine Receptor Antogonists" *J. Med. Chem.* 33:2822-2828 (1990).

Limori, et al., "2'-C-, 3'-C- and 5'-C-Methylsangivamycins: Conformational Lock With The Methyl Group," *Tetrahedrom Letters* 32(49) 7273-7276 (1991).

Kondo, et al., "Synthesis of 5-Methyltubercidin and Its α-Anomer via Condensation of the Anion of 4-methoxy-5-methyl-2-methylthiopyrrolo [2, 3-d] pyrimidine and 2, 3,5-Tri-O-benzyl-D-ribofuranosyl Bromide," *Agric.Biol. Chem.*41(8):1501-1507 (1977).

Uematsu, et al., "5-Hydroxymethyltubercidin, Synthesis, Biological Activity, and Role in Pyrrolopyrimidine Biosynthesis," *J. of Med. Chem*, 16(12):1405-1407(1973).

Schram, et al., "Pyrrolopyrimidine Nucleosides VIII. Synthesis of Sangivamycin Derivatives possessing exocyclic heterocycles at C 5" *J. Carbohydrates, Nucleosides, Nucleotides* 1(1):39-54 (1974).

Murai et al. "A Synthesis and an X-Ray Analysis of 2'-C,3'-C- And 5'-C-Methylsangivamycins" *Heterocycles* 33:391-404 (1992).

Beigelman et al. "New Syntheses of 2'-C-Methylnucleosides Starting from D-Glucose and D-Ribose" *Carbo. Research*, 166:219-232 (1987).

* cited by examiner

NUCLEOSIDE COMPOUNDS FOR TREATING VIRAL INFECTIONS

CROSS-REFERENCE TO RELATED APPLICATIONS

This application claims the benefit under 35 U.S.C. 119(e) of U.S. Provisional Patent Application Ser. No. 60/515,153 filed Oct. 27, 2003 which application is incorporated herein by reference in its entirety.

FIELD OF THE INVENTION

The invention relates to the field of pharmaceutical chemistry, in particular to compounds, compositions and methods for treating viral infections in mammals mediated, at least in part, by a virus in the flaviviridae family of viruses.

REFERENCES

The following publications are cited in this application as superscript numbers:
1. Giangaspero, et al., Arch. Virol. Suppl., 7: 53–62 (1993);
2. Giangaspero, et al., Int. J. STD. AIDS, 4(5): 300–302 (1993);
3. Yolken, et al., Lancet, 1(8637): 517–20 (1989);
4. Wilks, et al., Lancet, 1(8629): 107 (1989);
5. Giangaspero, et al., Lancet, 2: 110 (1988);
6. Potts, et al., Lancet, 1(8539): 972–973 (1987);
7. Cornberg, et al., "Hepatitis C: therapeutic perspectives." Forum (Genova), 11(2):154–62 (2001);
8. Dymock, et al., Antivir. Chem. Chemother. 11(2):79–96 (2000);
9. Devos, et al., International Patent Application Publication No. WO 02/18404 A2, published 7 Mar., 2002;
10. Sommadossi, et al., International Patent Application Publication No. WO 01/90121, published 23 May, 2001;
11. Carroll, S. S., et al., International Patent Application Publication No. WO 02057287, published 25 Jul., 2002;
12. Carroll, S. S., et al., International Patent Application Publication No. WO 02057425, published 25 Jul., 2002;
13. Herr, J. R., Bioorg. Med. Chem., 10: 3379–3393 (2002);
14. Andersen, K. E. et al., Eur. J. Med. Chem, 31: 417–425 (1996);
15. Thomber, C. W. Chem. Soc. Rev. 8: 563–580 (1979);
16. Lipinski, C. A. Annual Reports in Med. Chem. 21: 283–297 (1986);
17. Wissner, A. et al., J. Med. Chem. 23: 715–717 (1980);
18. Patani, G. A. et al., Chem. Rev. 96: 3147–3176 (1996).

All of the above publications and applications are herein incorporated by reference in their entirety to the same extent as if each individual publication or application was specifically and individually indicated to be incorporated by reference in its entirety.

State of the Art

The Flaviviridae family of viruses is composed of three genera: pestivirus, flavivirus and hepacivirus (hepatitis C virus). Of these genera, flaviviruses and hepaciviruses represent important pathogens of man and are prevalent throughout the world. There are 38 flaviviruses associated with human disease, including the dengue fever viruses, yellow fever virus and Japanese encephalitis virus. Flaviviruses cause a range of acute febrile illnesses and encephalitic and hemorrhagic diseases. Hepaciviruses currently infect approximately 2 to 3% of the world population and cause persistent infections leading to chronic liver disease, cirrhosis, hepatocellular carcinoma and liver failure. Human pestiviruses have not been as extensively characterized as the animal pestiviruses. However, serological surveys indicate considerable pestivirus exposure in humans. Pestivirus infections in man have been implicated in several diseases including, but not likely limited to, congenital brain injury, infantile gastroenteritis and chronic diarrhea in human immunodeficiency virus (HIV) positive patients.[1-6]

Currently, there are no antiviral pharmaceutical drugs to prevent or treat pestivirus or flavivirus infections. For hepacivirus, i.e, hepatitis C virus (HCV) infections, interferon alpha (IFN) is currently the only approved drug in the United States. HCV is a major causative agent for post-transfusion and for sporadic non-A, non-B hepatitis. Infection by HCV is insidious in a high proportion of chronically infected (and infectious) carriers who may not experience clinical symptoms for many years.

At present, the only acceptable treatment for chronic HCV is interferon (IFN-alpha) and this requires at least six (6) months of treatment and/or ribavarin, which can inhibit viral replication in infected cells and also improve liver function in some people.

SUMMARY OF THE INVENTION

This invention is directed to novel compounds that are useful in the viral infections in mammals, mediated at least in part by a virus in the flaviviridae family of viruses. Specifically, the compounds of this invention are represented by Formula I below:

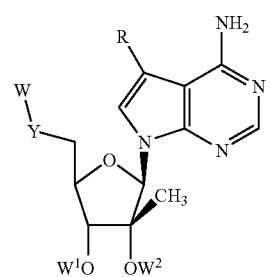

wherein Y is selected from the group consisting of a bond, —CH$_2$— or —O—;

each of W, W$^1$ and W$^2$ is independently selected from the group consisting of hydrogen and a pharmaceutically acceptable prodrug;

R is —C≡C-Q$^1$ or —CH=CH-Q$^2$;

Q$^1$ is selected from the group consisting of H, carboxyl, carboxyl ester, phenyl, and phenyl substituted with from 1 to 2 substituents selected from the group consisting of methyl, ethyl, and halo; and Q$^2$ is selected from hydrogen or cis-methoxy;

or pharmaceutically acceptable salts or partial salts thereof.

Particularly preferred compounds of the present invention are encompassed in Formula II to Formula V below (or pharmaceutically acceptable salts or partial salts thereof), wherein Y, W, W$^1$ and W$^2$ are as defined above.

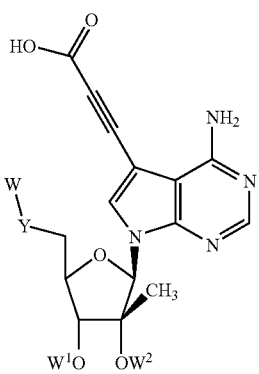

II

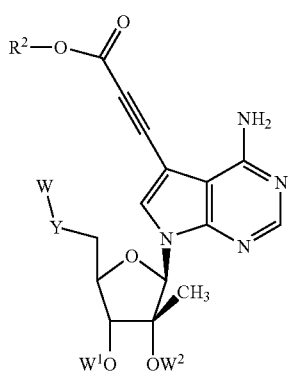

III

In Formula III R² is alkyl.

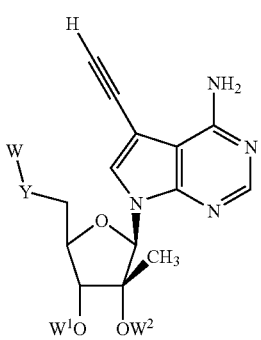

IV

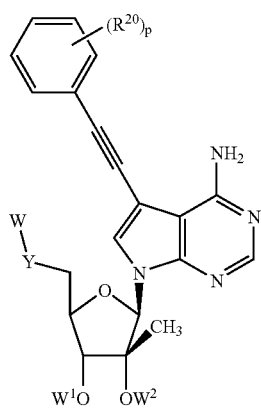

V

In Formula V, R²⁰ is selected from the group consisting of hydrogen, carboxyl, carboxyl esters, phenyl, and phenyl substituted with from 1 to 2 substitutents selected from the group consisting of methyl, ethyl, and halo; and p is 0, 1, or 2.

Preferably each of W, W¹, and W² is independently hydrogen or a pharmaceutically acceptable prodrug selected from the group consisting of acyl, oxyacyl, phosphonate, phosphate esters, phosphate, phospho, diphospho, triphospho, phosphonamidate, phosphorodiamidate, phosphoramidate monoester, cyclic phosphoramidate, cyclic phosphorodiamidate, phosphoramidate diester, and —C(O)CHR³NH₂, where R³ is a sidechain of an amino acid, or where W and W¹ may optionally join together to form a cyclic phosphonamidate.

In a particularly preferred embodiment, the compounds of this invention are represented by Formula VI below:

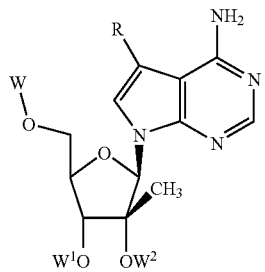

VI

In Formula VI, each of R, W, W¹ and W² is as defined above.

In still a further preferred embodiment, the compounds of this invention are represented by Formula VII–XIII as follows wherein each of R, W, W¹ and W² is as defined above:

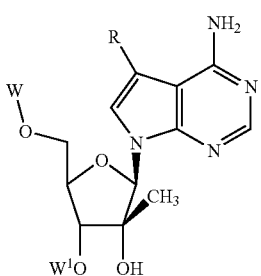

VII

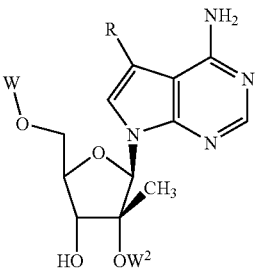

VIII

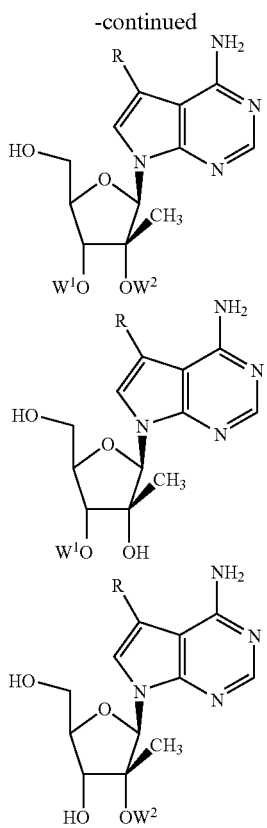

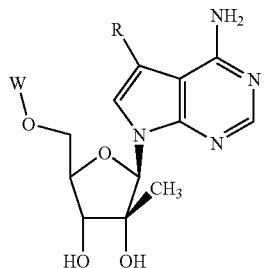

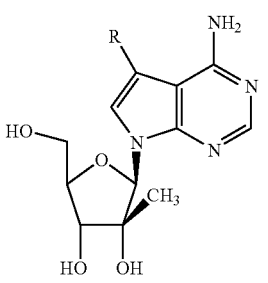

In the compounds of formulas I–VIII and XII, preferably W is hydrogen, phospho, diphospho, or triphospho.

Particularly preferred compounds of this invention include those set forth in the following Table I (including pharmaceutically acceptable salts or partial salts thereof):

TABLE I

| # | Structure | Name |
|---|-----------|------|
| 99 | 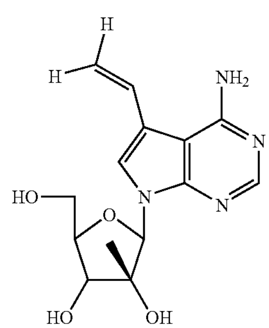 | 7-(2'-C-methyl-β-D-ribofuranosyl)-4-amino-5-(ethen-1-yl)-pyrrolo[2,3-d]pyrimidine |
| 100 | 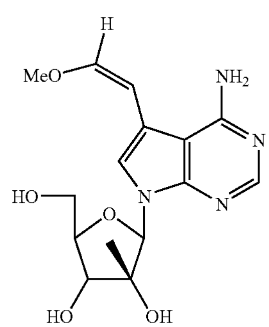 | 7-(2'-C-methyl-β-D-ribofuranosyl)-4-amino-5-(2-cis-methoxy-ethen-1-yl)-pyrrolo[2,3-d]pyrimidine |

TABLE I-continued

| # | Structure | Name |
|---|---|---|
| 101 | 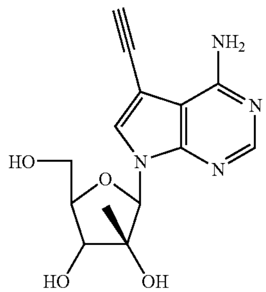 | 7-(2'-C-methyl-β-D-ribofuranosyl)-4-amino-5-(ethyn-1-yl)-pyrrolo[2,3-d]pyrimidine |
| 102 | 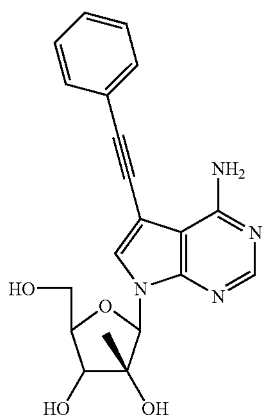 | 7-(2'-C-methyl-β-D-ribofuranosyl)-4-amino-5-(2-phenylethyn-1-yl)-pyrrolo[2,3-d]pyrimidine |
| 103 | 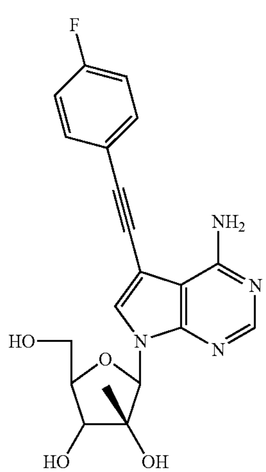 | 7-(2'-C-methyl-β-D-ribofuranosyl)-4-amino-5-(2-(4-fluorophenyl)ethyn-1-yl)-pyrrolo[2,3-d]pyrimidine |

TABLE I-continued

| # | Structure | Name |
|---|---|---|
| 104 | 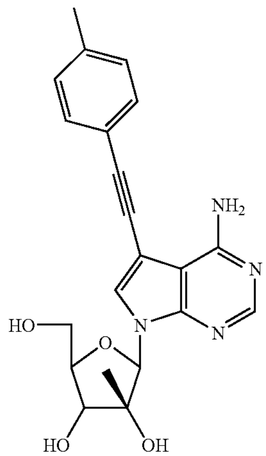 | 7-(2'-C-methyl-β-D-ribofuranosyl)-4-amino-5-(2-(4-methylphenyl)ethyn-1-yl)-pyrrolo[2,3-d]pyrimidine |
| 105 | 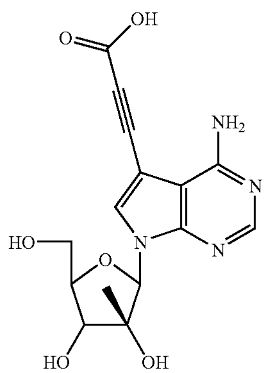 | 7-(2'-C-methyl-β-D-ribofuranosyl)-4-amino-5-(2-carboxyethyn-1-yl)-pyrrolo[2,3-d]pyrimidine |
| 106 | 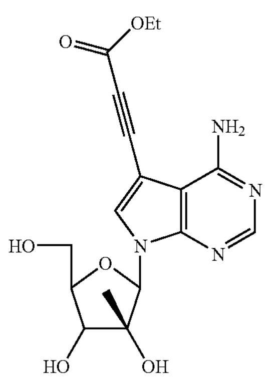 | 7-(2'-C-methyl-β-D-ribofuranosyl)-4-amino-5-[(ethyl 2-carboxyl)ethyn-1-yl]-pyrrolo[2,3-d]pyrimidine |
| 107 | 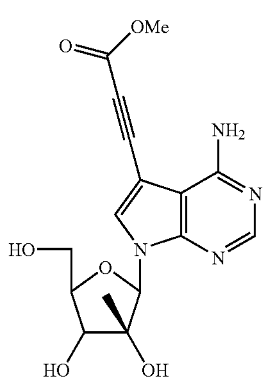 | 7-(2'-C-methyl-β-D-ribofuranosyl)-4-amino-5-[(methyl 2-carboxyl)ethyn-1-yl]-pyrrolo[2,3-d]pyrimidine |

TABLE I-continued

| # | Structure | Name |
|---|---|---|
| 108 | 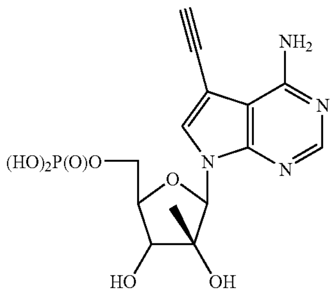 | 7-(2'-C-methyl-5'-phospho-β-D-ribofuranosyl)-4-amino-5-(ethyn-1-yl)-pyrrolo[2,3-d]pyrimidine |
| 109 | 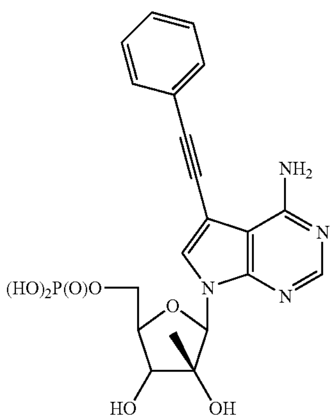 | 7-(2'-C-methyl-5'-phospho-β-D-ribofuranosyl)-4-amino-5-(2-phenylethyn-1-yl)-pyrrolo[2,3-d]pyrimidine |
| 110 | 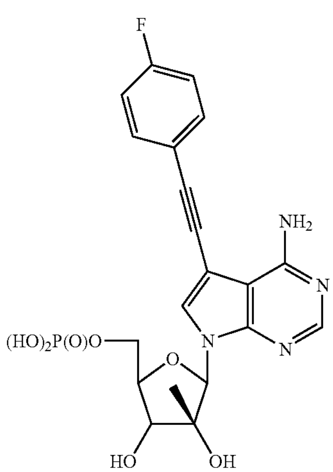 | 7-(2'-C-methyl-5'-phospho-β-D-ribofuranosyl)-4-amino-5-(2-(4-fluorophenyl)ethyn-1-yl)-pyrrolo[2,3-d]pyrimidine |

TABLE I-continued

| # | Structure | Name |
|---|---|---|
| 111 | 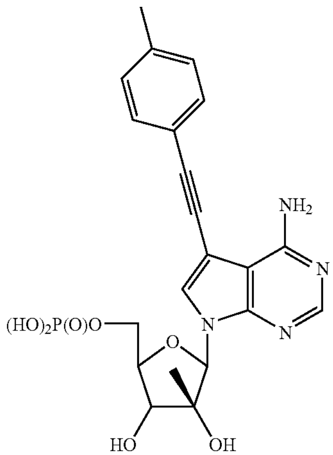 | 7-(2'-C-methyl-5'-phospho-β-D-ribofuranosyl)-4-amino-5-(2-(4-methylphenyl)ethyn-1-yl)-pyrrolo[2,3-d]pyrimidine |
| 112 | 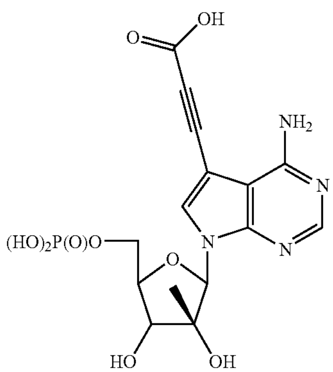 | 7-(2'-C-methyl-5'-phospho-β-D-ribofuranosyl)-4-amino-5-(2-carboxyethyn-1-yl)-pyrrolo[2,3-d]pyrimidine |
| 113 | 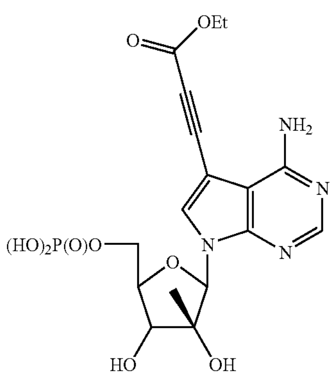 | 7-(2'-C-methyl-5'-phospho-β-D-ribofuranosyl)-4-amino-5-[(ethyl 2-carboxyl)ethyn-1-yl]-pyrrolo[2,3-d]pyrimidine |
| 114 | 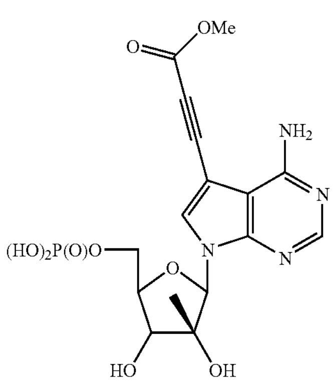 | 7-(2'-C-methyl-5'-phospho-β-D-ribofuranosyl)-4-amino-5-[(methyl 2-carboxyl)ethyn-1-yl]-pyrrolo[2,3-d]pyrimidine |

TABLE I-continued

| # | Structure | Name |
|---|---|---|
| 115 | 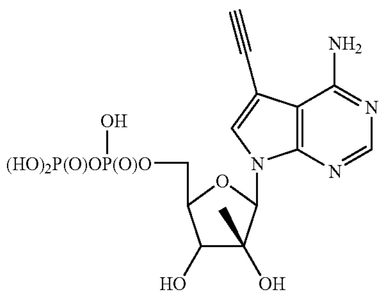 | 7-(2'-C-methyl-5'-diphospho-β-D-ribofuranosyl)-4-amino-5-[ethyn-1-yl]-pyrrolo[2,3-d]pyrimidine |
| 116 | 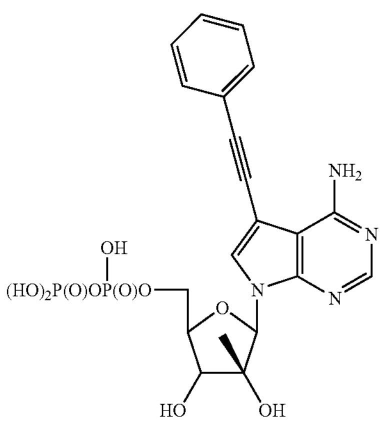 | 7-(2'-C-methyl-5'-diphospho-β-D-ribofuranosyl)-4-amino-5-(2-phenylethyn-1-yl)-pyrrolo[2,3-d]pyrimidine |
| 117 | 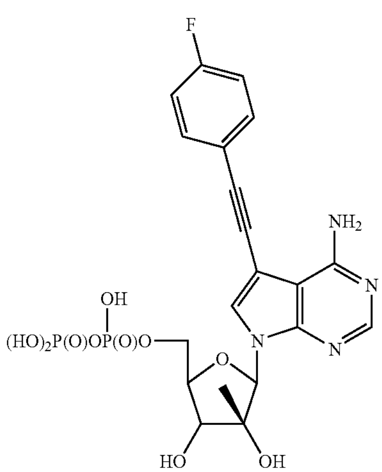 | 7-(2'-C-methyl-5'-diphospho-β-D-ribofuranosyl)-4-amino-5-(2-(4-fluorophenyl)ethyn-1-yl)-pyrrolo[2,3-d]pyrimidine |

TABLE I-continued

| # | Structure | Name |
|---|---|---|
| 118 | 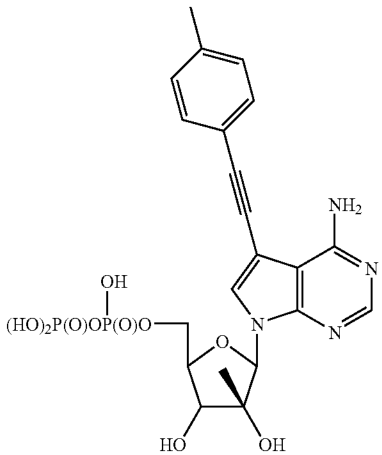 | 7-(2'-C-methyl-5'-diphospho-β-D-ribofuranosyl)-4-amino-5-(2-(4-methylphenyl)ethyn-1-yl)-pyrrolo[2,3-d]pyrimidine |
| 119 | 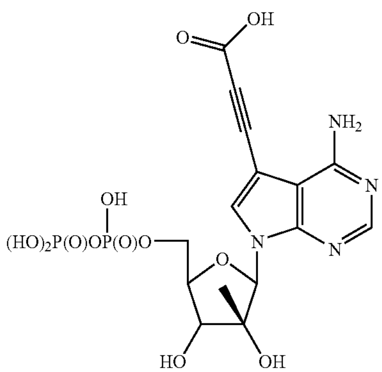 | 7-(2'-C-methyl-5'-diphospho-β-D-ribofuranosyl)-4-amino-5-(2-carboxyethyn-1-yl)-pyrrolo[2,3-d]pyrimidine |
| 120 | 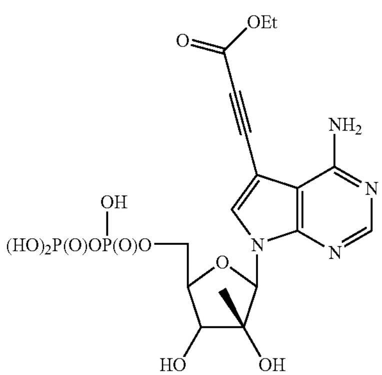 | 7-(2'-C-methyl-5'-diphospho-β-D-ribofuranosyl)-4-amino-5-[(ethyl 2-carboxyl)ethyn-1-yl]-pyrrolo[2,3-d]pyrimidine |
| 121 | 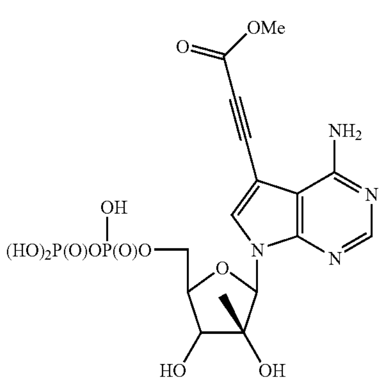 | 7-(2'-C-methyl-5'-diphospho-β-D-ribofuranosyl)-4-amino-5-[(methyl 2-carboxyl)ethyn-1-yl]-pyrrolo[2,3-d]pyrimidine |

TABLE I-continued

| # | Structure | Name |
|---|---|---|
| 122 | 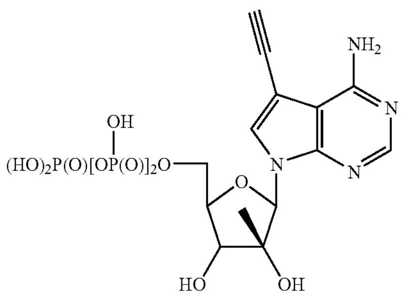 | 7-(2'-C-methyl-5'-triphospho-β-D-ribofuranosyl)-4-amino-5-(ethyn-1-yl)-pyrrolo[2,3-d]pyrimidine |
| 123 | 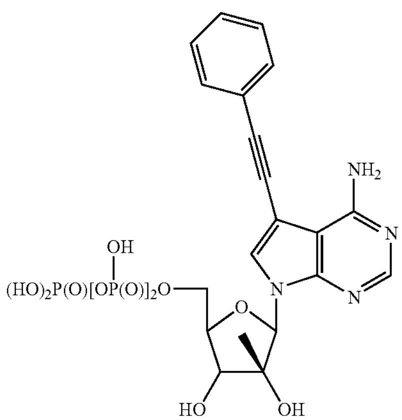 | 7-(2'-C-methyl-5'-triphospho-β-D-ribofuranosyl)-4-amino-5-(2-phenylethyn-1-yl)-pyrrolo[2,3-d]pyrimidine |
| 124 | 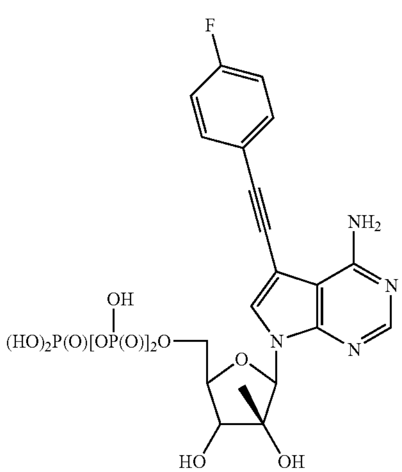 | 7-(2'-C-methyl-5'-triphospho-β-D-ribofuranosyl)-4-amino-5-(2-(4-fluorophenyl)ethyn-1-yl)-pyrrolo[2,3-d]pyrimidine |

TABLE I-continued

| # | Structure | Name |
|---|---|---|
| 125 | 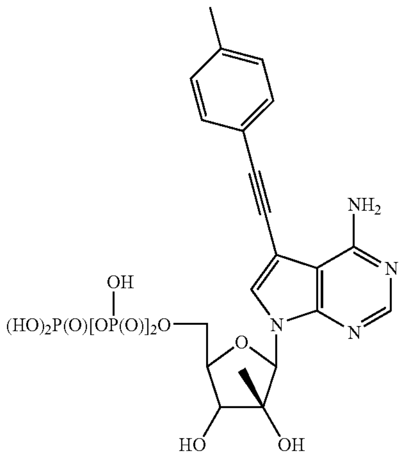 | 7-(2'-C-methyl-5'-triphospho-β-D-ribofuranosyl)-4-amino-5-(2-(4-methylphenyl)ethyn-1-yl)-pyrrolo[2,3-d]pyrimidine |
| 126 | 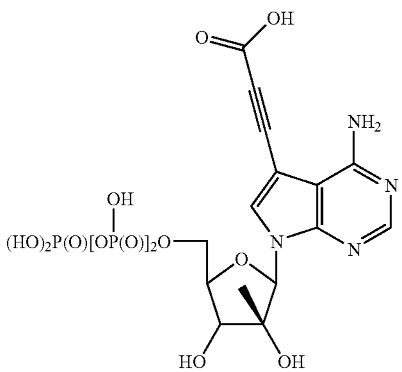 | 7-(2'-C-methyl-5'-triphospho-β-D-ribofuranosyl)-4-amino-5-(2-carboxyethyn-1-yl)-pyrrolo[2,3-d]pyrimidine |
| 127 | 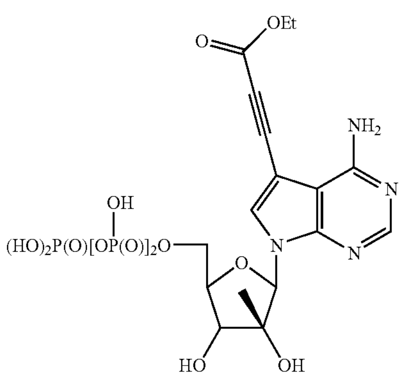 | 7-(2'-C-methyl-5'-triphospho-β-D-ribofuranosyl)-4-amino-5-[(ethyl 2-carboxyl)ethyn-1-yl]-pyrrolo[2,3-d]pyrimidine |
| 128 | 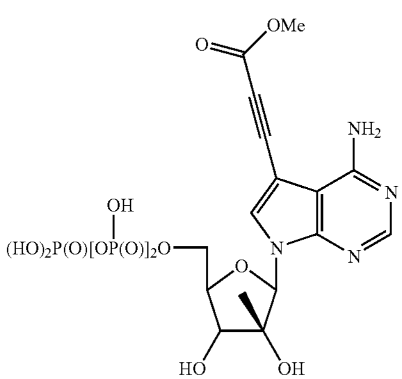 | 7-(2'-C-methyl-5'-triphospho-β-D-ribofuranosyl)-4-amino-5-[(methyl 2-carboxyl)ethyn-1-yl]-pyrrolo[2,3-d]pyrimidine |

TABLE I-continued

| # | Structure | Name |
|---|---|---|
| 129 | 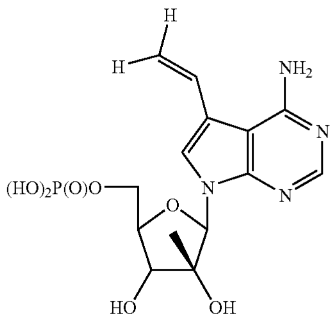 | 7-(2'-C-methyl-5'-monophospho-β-D-ribofuranosyl)-4-amino-5-(ethen-1-yl)-pyrrolo[2,3-d]pyrimidine |
| 130 | 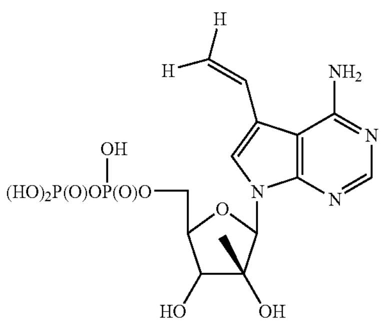 | 7-(2'-C-methyl-5'-diphospho-β-D-ribofuranosyl)-4-amino-5-(ethen-1-yl)-pyrrolo[2,3-d]pyrimidine |
| 131 | 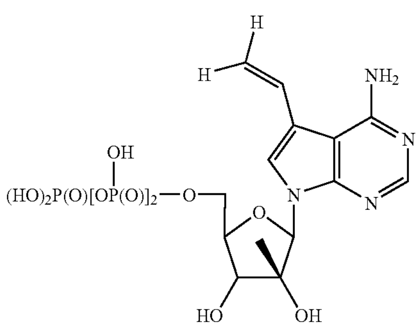 | 7-(2'-C-methyl-5'-triphospho-β-D-ribofuranosyl)-4-amino-5-(ethen-1-yl)-pyrrolo[2,3-d]pyrimidine |
| 132 | 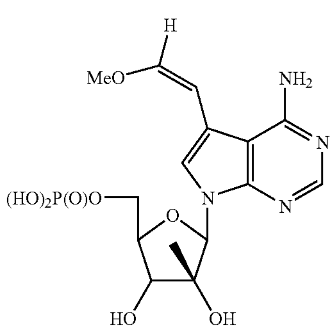 | 7-(2'-C-methyl-5'-monophospho-β-D-ribofuranosyl)-4-amino-5-(2-cis-methoxy-ethen-1-yl)-pyrrolo[2,3-d]pyrimidine |

TABLE I-continued

| # | Structure | Name |
|---|---|---|
| 133 | 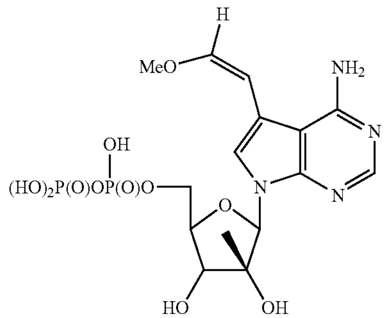 | 7-(2'-C-methyl-5'-diphospho-β-D-ribofuranosyl)-4-amino-5-(2-cis-methoxy-ethen-1-yl)-pyrrolo[2,3-d]pyrimidine |
| 134 | 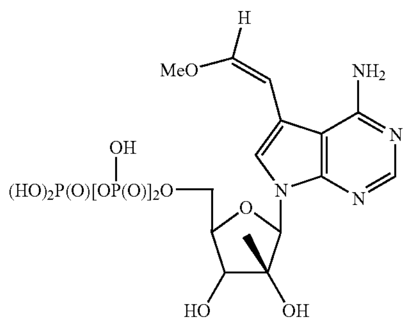 | 7-(2'-C-methyl-5'-triphospho-β-D-ribofuranosyl)-4-amino-5-(2-cis-methoxy-ethen-1-yl)-pyrrolo[2,3-d]pyrimidine |

Compounds of this invention are active as antiviral agents or useful as intermediates in the preparation of antiviral agents of Formula I–XIII This invention is also directed to pharmaceutical compositions comprising a pharmaceutically acceptable diluent and a therapeutically effective amount of a compound of Formula I–XIII or mixtures of one or more of such compounds.

This invention is still further directed to methods for treating a viral infection mediated at least in part by a virus in the flaviviridae family of viruses, such as HCV, in mammals which methods comprise administering to a mammal, that has been diagnosed with said viral infection or is at risk of developing said viral infection, a pharmaceutical composition comprising a pharmaceutically acceptable diluent and a therapeutically effective amount of a compound of Formula I–XIII or mixtures of one or more of such compounds.

In yet another embodiment of the invention, methods of treating or preventing viral infections in mammals are provided where in the compounds of this invention are administered in combination with the administration of a therapeutically effective amount of one or more agents active against HCV. Active agents against HCV include ribavirin, levovirin, thymosin alpha-1, an inhibitor of NS3 serine protease, and inhibitor of inosine monophosphate dehydrogenase, interferon-alpha, pegylated interferon-alpha, alone or in combination with ribavirin or levovirin. Preferably the additional agent active against HCV is interferon-alpha or pegylated interferon-alpha alone or in combination with ribavirin or levovirin.

DETAILED DESCRIPTION OF THE INVENTION

The invention is directed to compounds, compositions and methods for treating flaviviridae viruses, such as hepatitis C virus infections. However, prior to describing this invention in detail, the following terms will first be defined:

DEFINITIONS

As used herein, the term "alkyl" refers to alkyl groups having from 1 to 6 carbon atoms and more preferably 1 to 2 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Acylamino" refers to the group —C(O)NR⁴R⁴ where each R⁴ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R⁴ is joined to form together with the nitrogen atom a heterocyclic or substituted heterocyclic ring.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

"Oxyacyl" refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

"Alkenyl" refers to alkenyl group preferably having from 2 to 6 carbon atoms and more preferably 2 to 4 carbon atoms and having at least 1 and preferably from 1–2 sites of alkenyl unsaturation. Such groups are exemplified by vinyl (ethen-1-yl), allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom. Preferred substituted alkenyl groups are selected from, but not limit to, 2,2-difluoroethen-1-yl, 2-methoxyethen-1-yl, and the like.

It is understood that the term "substituted alkenyl" includes both E (cis) and Z (trans) isomers as appropriate. The isomers can be pure isomeric compounds or mixtures of E and Z components.

"Alkynyl" refers to an unsaturated hydrocarbon having at least 1 site of alkynyl unsaturation and having from 2 to 6 carbon atoms and more preferably 2 to 4 carbon atoms. Preferred alkynyl groups are selected from but not limit to ethyn-1-yl, propyn-1-yl, propyn-2-yl, 1-methylprop-2-yn-1-yl, butyn-1-yl, butyn-2-yl, butyn-3-yl, and the like.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. Preferred substituted alkynyl groups are selected from but not limit to 2-fluoroethyn-1-yl, 3,3,3-trifluoropropyn-1-yl, 3-aminopropyn-1-yl, 3-hydroxypropyn-1-yl, and the like.

"Amino" refers to the group —NH₂.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino.

"Aminoacyl" refers to the groups —NR⁵C(O)alkyl, —NR⁵C(O)substituted alkyl, —NR⁵C(O)cycloalkyl, —NR⁵C(O)substituted cycloalkyl, —NR⁵C(O)alkenyl, —NR⁵C(O)substituted alkenyl, —NR⁵C(O)alkynyl, —NR⁵C(O)substituted alkynyl, —NR⁵C(O)aryl, —NR⁵C(O)substituted aryl, —NR⁵C(O)heteroaryl, —NR⁵C(O)substituted heteroaryl, —NR⁵C(O)heterocyclic, and —NR⁵C(O)substituted heterocyclic where R⁵ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl", including "substituted phenyl" refers to aryl groups or phenyl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl esters" refers to the groups —C(O)O-alkyl, —C(O)O-substituted alkyl, —C(O)Oaryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo or iodo and preferably is fluoro or chloro.

"Heteroaryl" refers to an aromatic group of from 1 to 10 carbon atoms and 1 to 4 heteroatoms selected from the group consisting of oxygen, nitrogen, sulfur, —S(O)— and —SO$_2$— within the ring. Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an aromatic ring atom. Preferred heteroaryls include pyridyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, —S(O)—, and —S(O)$_2$— within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Phosphate" refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood, of course, that the initial oxygen of the mono-, di- and triphosphate (phospho, diphospho and triphospho) includes the oxygen atom at the 5-position of the ribose sugar.

"Phosphate esters" refers to the mono-, di- and tri-phosphate groups described above wherein one or more of the hydroxyl groups is replaced by an alkoxy group.

"Phosphonate" refers to the groups —OP(O)(R$^6$)(OH) or —OP(O)(R$^6$)(OR$^6$) or salts thereof including partial salts thereof, wherein each R$^6$ is independently selected from hydrogen, alkyl, substituted alkyl, carboxylic acid, and carboxyl ester. It is understood, of course, that the initial oxygen of the phosphonate includes the oxygen atom at the 5-position of the ribose sugar.

"Phosphorodiamidate" refers to the group:

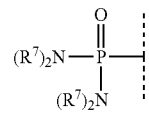

where each R$^7$ may be the same or different and each is hydrogen, alkyl, substituted alkyl, cycloalkyl, or substituted cycloalkyl. A particularly preferred phosphorodiamidate is the following group:

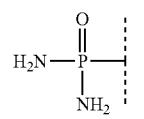

"Phosphoramidate monoester" refers to the group below, where R$^8$ is hydrogen or alkyl and R$^9$ may be the same or different and each is hydrogen, alkyl, substituted alkyl, cycloalkyl, or substituted cycloalkyl.

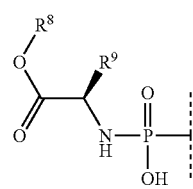

"Phosphoramidate diester" refers to the group below, where R$^8$ is hydrogen or alkyl, R$^{10}$ is aryl, substituted aryl, alkyl, or substutituted alkyl, and each R$^9$ is hydrogen, alkyl, substituted alkyl, cycloalkyl, and substituted cycloalkyl.

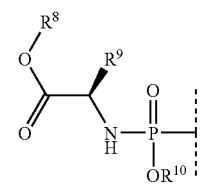

"Cyclic phosphorodiamidate" refers to the group below, where n is 1 to 3, more preferably n is 1 to 2.

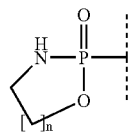

"Cyclic phosphorodiamidate" refers to the group below, where n is 1 to 3, more preferably n is 1 to 2.

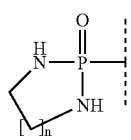

"Phosphonamidate" refers to the group below, where $R^{11}$ is hydrogen, alkyl, substituted alkyl, cycloalkyl, or substituted cycloalkyl.

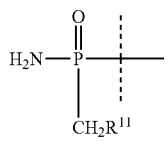

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thiocycloalkyl" refers to the groups —S-cycloalkyl and "substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

The term "amino acid sidechain" refers to the $R^{12}$ substituent of α-amino acids of the formula $R^{13}NHCH(R^{12})$ COOH where $R^{12}$ is selected from the group consisting of hydrogen, alkyl, substituted alkyl and aryl and $R^{13}$ is hydrogen or together with $R^{12}$ and the nitrogen and carbon atoms bound thereto respectively form a heterocyclic ring. Preferably, the α-amino acid sidechain is the sidechain one of the twenty naturally occurring L amino acids.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkyl-ammonium, and the like; and when the molecule contains a basic functionality, salts of organic or inorganic acids, such as hydrochloride, hydrobromide, tartrate, mesylate, acetate, maleate, oxalate and the like.

The term "pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1–15 (John Wiley and Sons, 1991), Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4$^{th}$ Edition), and Larock's Comprehensive Organic Transformations (VCH Publishers Inc., 1989). Specifically, the compounds of this invention may be prepared by various methods known in the art of organic chemistry in general and nucleoside and nucleotide analogue synthesis in particular. General reviews of the preparation of nucleoside and nucleotide analogues include 1) Michelson A. M. "*The Chemistry of Nucleosides and Nucleotides*," Academic Press, New York, 1963; 2) Goodman L. "*Basic Principles in Nucleic Acid Chemistry*," Academic Press, New York, 1974, vol. 1, Ch. 2; and 3) "*Synthetic Procedures in Nucleic Acid Chemistry*," Eds. Zorbach W. & Tipson R., Wiley, New York, 1973, vol. 1 & 2.

The synthesis of the compounds of this invention generally follows either a convergent or linear synthetic pathway as described below.

The strategies available for synthesis of compounds of this invention include for example:

General Synthesis of 2'-C-Branched Nucleosides

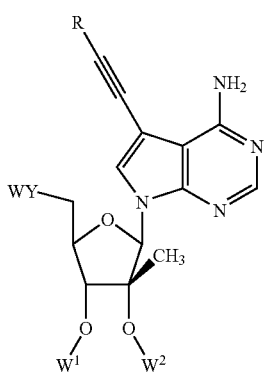

I

2'-C-Branched ribonucleosides of Formula I above, where R, W, W$^1$, and W$^2$ are as defined above, can be prepared by one of the following general methods.

Convergent Approach: Glycosylation of Nucleobase with Appropriately Modified Sugar The key starting material of this process is an appropriately substituted sugar with 2'-OH and 2'-H with the appropriate leaving group, for example, an acyl group or a chloro, bromo, fluoro or iodo group. The sugar can be purchased or can be prepared by any known means including standard epimerization, substitution, oxidation and/or reduction techniques. For example, commercially available 1,3,5-tri-O-benzoyl-α-D-ribofuranose (Pfanstiel Laboratories, Inc.) can be used. The substituted sugar can then be oxidized with the appropriate oxidizing agent in a compatible solvent at a suitable temperature to yield the 2'-modified sugar. Possible oxidizing agents are, for example, Dess-Martin periodine reagent, Ac$_2$O+ DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO$_2$, ruthenium tetraoxide, phase transfer catalysts such as chromic acid or permanganate supported on a polymer, Cl$_2$-pyridine, H$_2$O$_2$-ammonium molybdate, NaBrO$_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or R$^2$—SiMe$_3$ in TBAF with the ketone with the appropriate non-protic solvent at a suitable temperature, yields the 2'-methyl sugar. For example, CH$_3$MgBr/TiCl$_4$ or CH$_3$MgBr/CeCl$_3$ can be used as described in Wolfe et al. 1997. *J. Org. Chem.* 62: 1754–1759. The methylated sugar can be optionally protected with a suitable protecting group, preferably with an acyl, substituted alkyl or silyl group, by methods well known to those skilled in the art, as taught by Greene et al. *Protective Groups in Organic Synthesis*, John Wiley and Sons, Second Edition, 1991.

The optionally protected sugar can then be coupled to the purine base by methods well known to those skilled in the art, as taught by Townsend *Chemistry of Nucleosides and Nucleotides*, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

In addition to the above, the 2'-C-substituted sugars used in the synthetic methods described herein are well known in the art and are described, for example, by Sommadossi, et al.[5] and by Carrol, et al.[6] both of which are incorporated herein by reference in their entirety.

Scheme 1 below describes the alternative synthesis of a protected sugar that is useful for coupling to the bases described herein.

Scheme 1

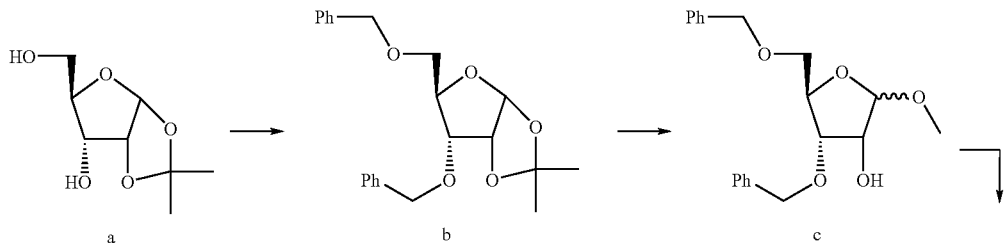

a    b    c

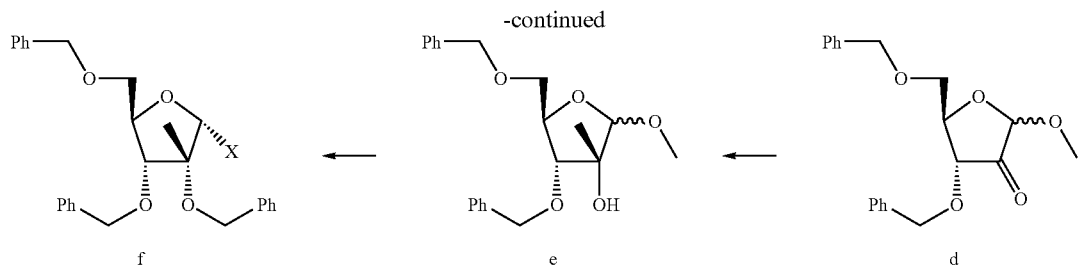

where Ph is phenyl and X is suitable leaving group such as halo

Formation of sugar a in Scheme 1, above, is accomplished as described by Mandal, S. B., et al., *Synth. Commun.*, 1993, 9, page 1239, starting from commercial D-ribose. Protection of the hydroxyl groups to form sugar b is described in Witty, D. R., et al., *Tet. Lett.*, 1990, 31, page 4787. Sugar c and d are prepared using the method of Ning, J. et al., *Carbohydr. Res.*, 2001, 330, page 165, and methods described herein. Sugar e is prepared by using a modification of the Grignard reaction with $CH_3MgBr$ or other appropriate organometallic as described herein (with no titanium/cerium needed). Finally the halogenated sugar (X=halo) used in the subsequent coupling reaction is prepared using the same protection method as used in to make sugar b above. The halogenation is described in Seela.[7]

Subsequently, any of the described nucleosides can be deprotected by methods well known to those skilled in the art, as taught by Greene et al. *Protective Groups in Organic Synthesis*, Jon Wiley and Sons, Second Edition, 1991.

An alternative approach to making protected sugars useful for coupling to heterocyclic bases is detailed in Scheme 2 below.

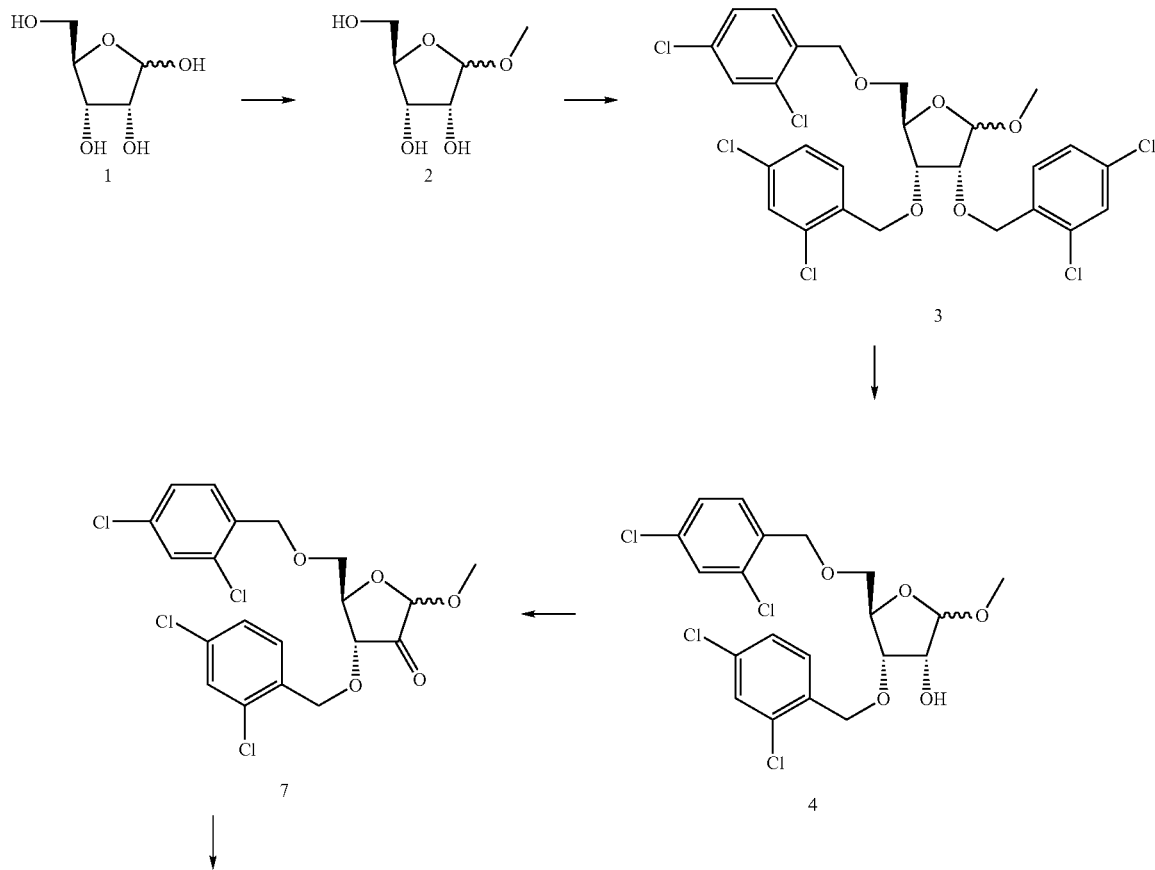

Scheme 2

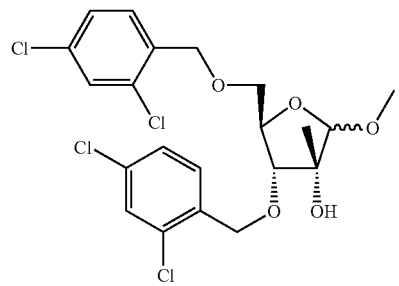

8

In Scheme 2, methylation of the hydroxyl group of compound 1 proceeds via conventional methodology to provide for compound 2. The 2, 3 and 5 hydroxyl groups of the compound 2 are each protected with 2,4-dichlorobenzyl groups to provide for compound 3. Selective deprotection of the 2-(2',4'-dichlorobenzyl) group on compound 3 proceeds via contact with stannous chloride in a suitable solvent such as methylene chloride, chloroform, and the like at reduced temperatures, e.g., ~0 to 5° C., until reaction completion, e.g., 24–72 hours. Oxidation of the 2-hydroxyl group proceeds as described herein to provide for compound 7. Methylation also proceeds as described herein to provide for compound 8.

Linear Approach: Modification of a Pre-formed Nucleoside

The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl, substituted alkyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are, for example, Dess-Martin periodine reagent, $Ac_2O$+ DCC in DMSO, Swern oxidation (DMSO, oxalyl chloride, triethylamine), Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$ ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Coupling of an organometallic carbon nucleophile, such as a Grignard reagent, an organolithium, lithium dialkylcopper or $CH_3SiMe_3$ in TBAF with the ketone with the appropriate non-protic solvent at a suitable temperature, yields the alkyl substituted nucleoside. Isolation of the appropriate isomer is conducted as needed.

Subsequently, the nucleoside can be deprotected by methods well known to those skilled in the art, as taught by Greene et al. *Protective Groups in Organic Synthesis*, John Wiley and Sons, Second Edition, 1991.

In one embodiment of the invention, the D-enantiomers are preferred. However, L-enantiomers are also contemplated to be useful herein. The L-enantiomers corresponding to the compounds of the invention can be prepared following the same foregoing general methods, beginning with the corresponding L-sugar or nucleoside as starting material. In a particular embodiment, the 2'-C-branched ribonucleoside is desired.

The compounds of this invention may be prepared by various methods known in the art of organic chemistry in general and nucleoside and nucleotide analogue synthesis in particular. The starting materials for the syntheses are either readily available from commercial sources or are known or may be prepared by techniques known in the art. General reviews of the preparation of nucleoside and nucleotide analogues are included in the following:

Michelson A. M. "*The Chemistry of Nucleosides and Nucleotides*," Academic Press, New York, 1963.

Goodman L. "*Basic Principles in Nucleic Acid Chemistry*," Academic Press, New York, 1974, vol. 1, Ch. 2.

"*Synthetic Procedures in Nucleic Acid Chemistry*," Eds. Zorbach W. & Tipson R., Wiley, New York, 1973, vol. 1 & 2.

The 5-acetylenyl-pyrrolo[2,3-d]pyrimidinyl nucleoside derivatives of the present invention can be synthesized using one or more of the methods depicted in Schemes 3, 4 and 5 below.

A convergent approach for preparing the pyrrolo[2,3-d] pyrimidinyl nucleosides is shown in Scheme 3 below. First commercially available 4-chloropyrrolo[2,3-d]pyrimidine 11 is halogenated at the 5-position (compound 12) using well known methods, for example, the halogenation method described in A. Gangjee et al., J. Med. Chem. (2003) 46, 591. Intermediate compound 12 may be isolated and purified using standard techniques such as chromatography, precipitation, crystallization, filtration, and the like. Alternatively, compound 12 may be isolated and used in the next step without further purification.

5-(Alkynyl)-4-chloropyrrolo[2,3-d]pyrimidine 13 is prepared using Sonigashira conditions as described in A. Gangjee et al., (J. Med. Chem. (2003) 46, 591) to yield compound 13. Intermediate compound 13 may be isolated and purified using standard techniques such as chromatography, precipitation, crystallization, filtration, and the like. Alternatively compound 13 may be isolated and used in the next step without further purification.

Compound 13 is coupled to protected 2-methyl substituted sugar 8 (the synthesis of which is described above and by Carrol, et al.,[11,12]) using conditions well known in the art.

For example, 1-O-methyl-3,5-bis-O-(2,4-dichlorophenylmethyl)-2'-C-methyl-β-D-ribofuranoside 8 is dissolved in a dry inert solvent, such as dichloromethane, chloroform, to about 48 hours. Compound 17 is isolated and purified using standard techniques such as chromatography, precipitation, crystallization, filtration, and the like.

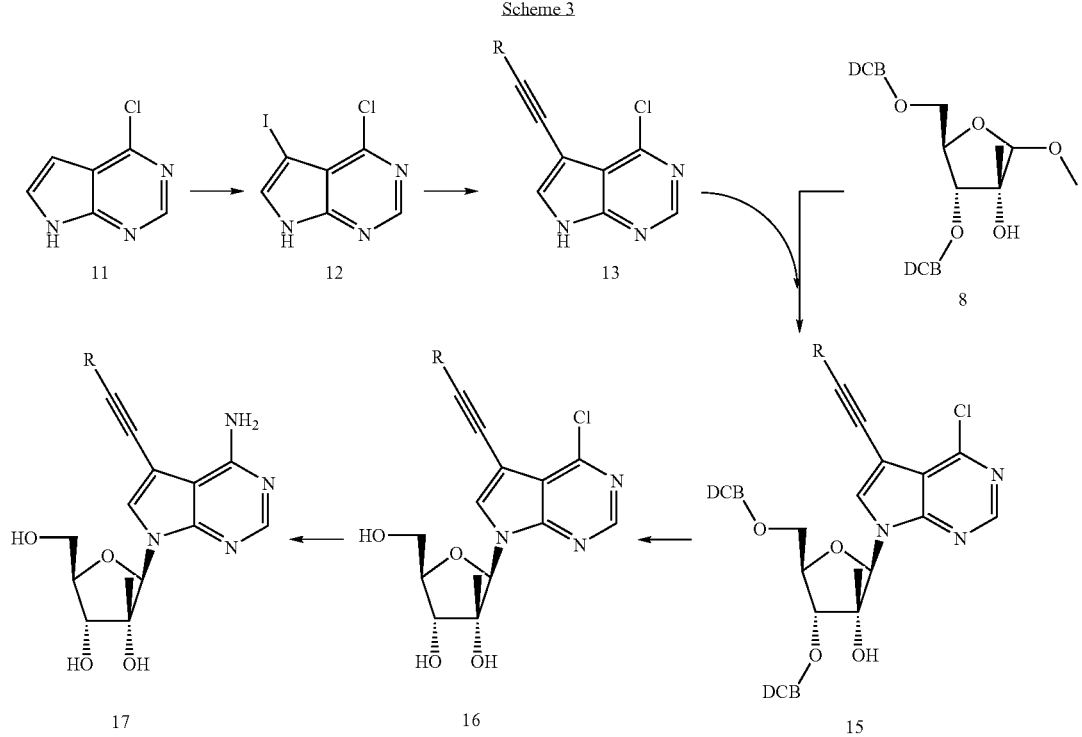

Scheme 3 where R is as defined herein and DCB is 2,4-dichlorobenzyl.

carbon tetrachloride and the like, and then the solution is cooled to about 0° C. Afterwards, an excess of HBr or other appropriate reagent, in acetic acid, is added drop wise. This reaction is run for typically at about 0° C. for about 1 hour or at ambient temperature for about 2.5 hours or until substantially complete as determined by conventional techniques such as tlc. The resulting brominated sugar mixture is isolated and purified using standard techniques such as chromatography, precipitation, crystallization, filtration, and the like. Alternatively this intermediate may be isolated and used in the next step without further purification. The resulting brominated sugar mixture is co-evaporated, preferably with dry toluene, dissolved in a suitable inert diluent such as dry acetonitrile and stirred with the sodium salt of compound 13 at room temperature over night. The sodium salt of compound 13 is prepared in an inert atmosphere by suspending compound 13 in a dry inert solvent such as, acetonitrile and the like, with NaH dispersed in oil. The reaction is run for about 2 to about 24 hours at a temperature of about 0 to about 40° C. Finally compound 15 is isolated and purified using standard techniques such as chromatography, precipitation, crystallization, filtration, and the like. Alternatively, this intermediate may be isolated and used in the next step without further purification.

Deprotection of compound 15 using standard methods affords compound 16, which is converted to the 4-amino derivative (compound 17) using methods well known in the art. For example, compound 16 is added to liquid ammonia at about −80° C. and is warmed to about 80° C. for about 24

In an alternative approach, the 1-[5-(alkynyl)-4-aminopyrrolo [2,3-d]pyrimidine]-2'-C-methyl-β-D-ribofuranoside compounds can be prepared using the method illustrated in Scheme 4 below.

Compound 12, prepared as described above is coupled to the protected sugar 8, using the techniques described for the preparation of compound 15 in Scheme 3 above to provide for compound 19. Deprotection of compound 19, using standard methods, provides compound 20.

From compound 20, the 1-[5-(alkynyl)-4-amino-pyrrolo [2,3-d]pyrimidine]-2'-C-methyl-β-D-ribofuranoside compounds can be prepared by first converting the 4-chloro group to an amino group, using the technique described for the preparation of compound 17 from compound 16 in scheme 3 above to provide for compound 21, followed by coupling using Sonigashira conditions as described in A. Gangjee et al., (J. Med. Chem. (2003) 46, 591) to form the 7-alkynyl derivative, compound 17.

Alternatively, from compound 20, the 1-[5-(alkynyl)-4-amino-pyrrolo[2,3-d]pyrimidine]-2'-C-methyl-β-D-ribofuranoside compounds can be prepared by first converting the 5-iodo group to the the 5-alkynyl derivative (compound 16), followed by conversion of the 4-chloro group to the amine (compound 17). The methods for each of these transformations is detailed above.

Scheme 4
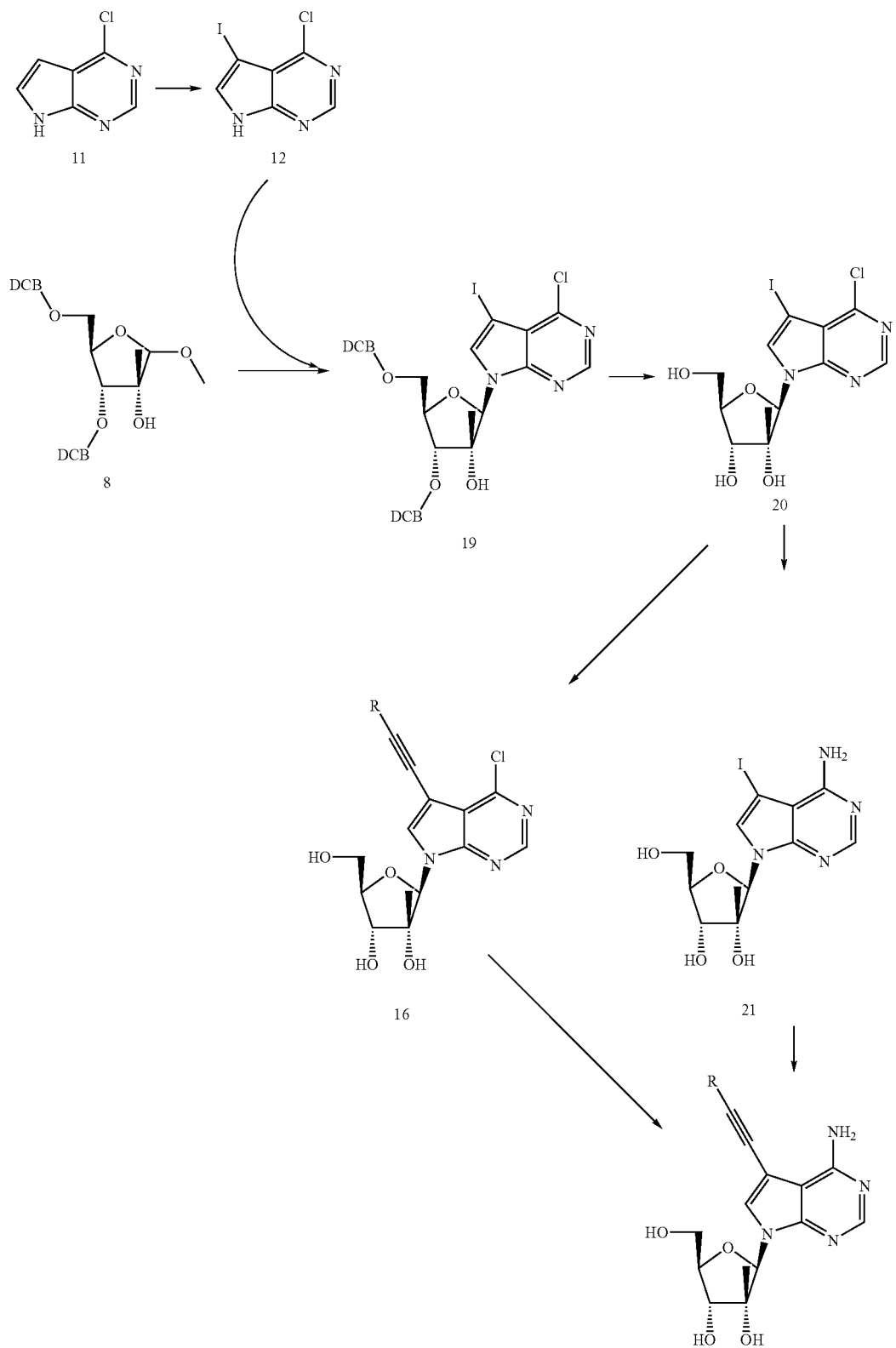
where R and DCB are as described above.

Preparation of compounds where W, $W^1$ or $W^2$ is other than hydrogen, using the compounds prepared in Schemes 3, 4 and 5 above as the starting materials, can be accomplished using the methods described in the following reviews of prodrug preparation:
1) Cooperwood, J. S. et al., "*Nucleoside and Nucleotide prodrugs,*" in Ed(s) Chu, C. K. Recent Advances in Nucleosides (2002), 92–147.
2) Zemlicka, J. et al., Biochimica et Biophysica Acta (2002), 158(2–3), 276–286.
3) Wagner, C. et al., Medicinal Research Reviews (2002), 20(6), 417–451.
4) Meier, C. et al., Synlett (1998), (3), 233–242.

For example, conversion of the 5'-hydroxyl group of the 1-[5-(alkynyl)-4-amino-pyrrolo[2,3-d]pyrimidine]-2'-C-methyl-β-D-ribofuranoside compounds to a phospho, diphospho or triphospho-analog can prepared using the methods describe in D. W. Hutchinson, (Ed. Leroy b. Townsend) "The Synthesis, reaction and Properties of Nucleoside Mono-, Di-, Tri-, and tertaphosphate and Nucleosides with Changes in the Phosphoryl Residue, "Chemistry of Nucleosides and Nucleotides, Plenum Press, (1991) 2.

Utility, Testing, and Administration

Utility

The present invention provides novel compounds possessing antiviral activity, including hepatitis C virus. The compounds of this invention inhibit viral replication by inhibiting the enzymes involved in replication, including RNA dependent RNA polymerase. They may also inhibit other enzymes utilized in the activity or proliferation of viruses in the flaviviridae family, such as HCV.

The compounds of the present invention can also be used as prodrug nucleosides. As such they are taken up into the cells and can be intracellularly phosphorylated by kinases to the triphosphate and are then inhibitors of the polymerase (NS5b) and/or act as chain-terminators.

Compounds of this invention may be used alone or in combination with other compounds to treat viruses.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula I may range from approximately 0.05 to 50 mg per kilogram body weight of the recipient per day; preferably about 0.01–25 mg/kg/day, more preferably from about 0.5 to 10 mg/kg/day. Thus, for administration to a 70 kg person, the dosage range would most preferably be about 35–70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract, in particular for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices—nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art.

Typically, the formulation will contain, on a weight percent (wt %) basis, from about 0.01–99.99 wt % of a compound of Formula I based on the total formulation, with the balance being one or more suitable pharmaceutical excipients. Preferably, the compound is present at a level of about 1–80 wt %. Representative pharmaceutical formulations containing a compound of Formula I are described below.

Additionally, the present invention is directed to a pharmaceutical composition comprising a therapeutically effective amount of a compound of the present invention in combination with a therapeutically effective amount of another active agent against RNA-dependent RNA virus and, in particular, against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffman-LaRoche, Nutley, N.J.), interferon-α2b (such as Intron-A interferon available from Schering Corp., Kenilworth, N.J., USA), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.*, 35:201–210 (2000).

EXAMPLES

The examples below as well as throughout the application, the following abbreviations have the following meanings. If not defined, the terms have their generally accepted meanings.

| | |
|---|---|
| AcOH or HOAc = | acetic acid |
| Ac$_2$O = | acetic anhydride |
| Ar = | aryl hydrogen |
| CAN = | ceric ammonium nitrate |
| cm = | centimeter |
| DCB = | 2,4-dichlorobenzyl |
| DCC = | dicyclohexylcarbodiimide |
| DMEM = | Delbecco's minimum eagles medium |
| DMSO = | dimethylsulfoxide |
| DTT = | dithiothreitol |
| EDTA = | ethylene diamine tetraacetic acid |
| eq. or eq = | equivalents |
| g = | gram |
| h or hr = | hour |
| HCV = | hepatitis C virus |
| IPTG = | Isopropyl β-D-1-thiogalactopyranoside |
| IU = | international units |
| L = | liters |
| m = | multiplet |
| M = | molar |
| Me = | methyl |
| mg = | milligram |
| mL = | milliliter |
| mm = | millimeters |
| mM = | millimolar |
| mmol = | millimol |
| MS = | mass spectrum |
| ng = | nanograms |
| nm = | nanometers |
| nM = | nanomolar |
| NMR = | nuclear magnetic resonance |
| NTP = | nucleotide triphosphate |
| RP HPLC = | reverse phase high performance liquid chromatography |
| s = | singlet |
| TFA = | trifluoroacetic acid |
| THF = | tetrahydrofuran |
| tlc = | thin layer chromatography |
| T$_m$ = | Melting temperature |
| UTP = | uridine triphosphate |
| μL = | microliters |
| μg = | micrograms |
| μM = | micromolar |
| v/v = | volume to volume |
| w/w = | weight to weight |
| wt % = | weight percent |

In addition, all reaction temperatures are in degrees Celsius and all percentages are molar percents unless reported otherwise.

In the examples below as well as elsewhere throughout this application, the claimed compounds employ the following numbering system:

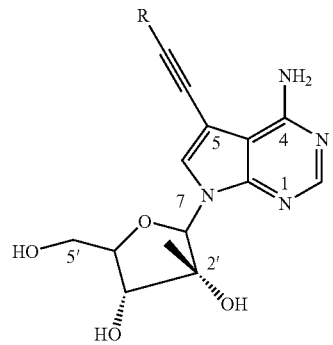

Example 1

Preparation of the intermediate 1-O-methyl-2-methyl-3,5-bis-O-(2,4-dichlorobenzyl)-β-D-ribofuiranose

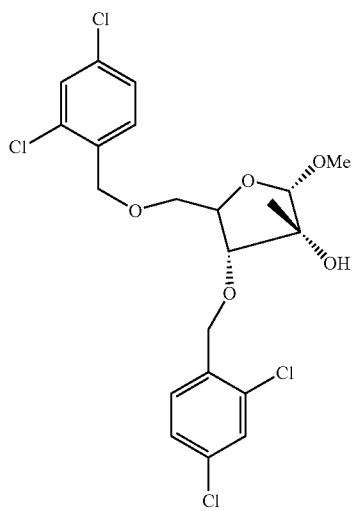

Step 1: Preparation of 1-O-methyl-2,3,5-tris-O-(2,4-dichlorobenzyl)-β-D-ribofuranose The title compound is synthesized using the methods described in Marin, P.; *Helv. Chim. Acta*, 1995, 78, 486 starting with commercially available D-ribose.

Step 2: Preparation of 1-O-methyl-3,5-bis-O-(2,4-dichlorobenzyl)-β-D-ribofuranose To a solution of the product of Step 1 (171.60 g, 0.2676 mol) in 1.8 L of methylene chloride that was cooled to 0° C., was added dropwise a solution of stannous chloride (31.522 mL, 0.2676 mol) in 134 mL of methylene chloride while stirring. After maintaining the solution at about 3° C. for approximately 27 hours, another 5.031 mL of stannous chloride ($SnCl_4$) (0.04282 mol) was added and the solution was kept at about 3° C. overnight. After a total reaction time of approximately 43 hours, the reaction was quenched by carefully adding the solution to 1.9 L of a saturated $NaHCO_3$ solution. Tin salts were removed via filtration through Celite after which the organic phase was isolated, dried with $MgSO_4$ and evaporated in vacuo. The yield of raw, dark yellow oil was 173.6 g. The crude oil was used directly in the next step without further purification.

Step 3: Preparation of 1-O-methyl-2-oxo-3,5-bis-O-(2,4-dichlorobenzyl)-β-D-ribofuranose To an ice cold solution of Dess-Martin periodinane (106.75 g, 0.2517 mol) in 740 mL anhydrous methylene chloride, under argon, was added a solution of the product of Step 2 above in 662 mL anhydrous methylene chloride over 0.5 hours. The reaction mixture was stirred at 0° C. for 0.5 hours and then at room temperature for 6 days. The mixture was diluted with 1.26 L of anhydrous diethyl ether and then poured into an ice-cold mixture of $Na_2S_3O_3 \cdot 5H_2$ (241.2 g, 1.5258 mol) in 4.7 L of saturated aqueous sodium bicarbonate. The layers were separated, and the organic layer was washed with 1.3 L of saturated aqueous sodium bicarbonate, 1.7 L water and 1.3 L brine, dried with $MgSO_4$, filtered and evaporated to give the target compound. The compound (72.38 g, 0.1507 mol) was used without further purification in the next step.

Step 4: Preparation of the Title Compound

A solution of MeMgBr in 500 mL anhydrous diethyl ether maintained at −55° C. was added dropwise to a solution of the product of step 3 above (72.38 g, 0.1507 mol) also in 502 mL of anhydrous diethyl ether. The reaction mixture was allowed to warm to −30° C. and stirred mechanically for 4 hours at from −30° C. to −15° C., then poured into 2 L ice cold water. After stirring vigorously at ambient temperature for 0.5 hours, the mixture was filtered through a Celite pad (14×5 cm), which was thoroughly washed with diethyl ether. The organic layer was dried with $MgSO_4$, filtered and concentrated in vacuo. The residue was dissolved in hexanes (~1 mL per gram crude), applied to a silica gel column (1.5 L silica gel in hexanes) and eluted with hexanes and 4:1 hexanes:ethyl acetate (v/v) to give 53.58 g (0.1080 mol) of the final purified product. The morphology of the title compound was that of an off-yellow, viscous oil.

MS: m/z 514.06 (M+$NH_4$+).

Example 2

Preparation of 7-(2'-C-methyl-β-D-ribofaranosyl)-4-amino-5-(ethyn-1-yl)-pyrrolo[2,3-d]pyrimidine Step 1. 4-Chloro-5-iodo-7H-pyrrolo[2,3-d]pyrimidine 4-Chloro-7H-pyrrolo[2,3-d]pyrimidine 10.75 g (70 mmol) and N-iodosuccinimide (16.8 g, 75 mmol) were dissolved in 400 mL of dry DMF and left at ambient temperature in the darkness over night. The solvent was evaporated. The yiellow residue was suspended in hot 10% solution of $Na_2SO_3$, filtered, washed twice with hot water and crystallized from ethanol to yield 14.6 g (74.6%) of the title compound as off-white crystals. The mother liquid was evaporated up to ⅓ volume and crystallize again from ethanol to give 2.47 g (12.3%) of the title product. The total yield is close to 100%.

$T_m$ 212–214 (dec)
UV $\lambda_{max}$: 307, 266, 230, 227 nm (methanol)
MS: 277.93 (M−H), 313 (M+Cl)
$^1$H-NMR (DMSO-d6): 12.94 (s, 1H, NH), 8.58 (s, 1H, H-2), 7.94 (s, 1H, H-8)

Step 2. 7-(2'-methyl-3',5'-bis-O-(2,4-dichlorobenzyl)-β-D-ribofuranosyl)-4-chloro-5-iodo-pyrrolo[2,3-d]pyrimidine The base, obtained as described above (11.2 g, 40 mmol) was suspended in 500 mL of $CH_3CN$, NaH was added (1.6 g, 40 mmol 60% in oil) and the reaction mixture was stirred at room temperature until NaH was dissolved (about 2 hour). 1-O-Methyl-2-methyl-3,5-bis-O-(2,4-dichlorobenzyl)-β-D-ribofuranose (10 g, 20 mmol) was dissolved in 500 mL of DCM and cooled down to 4° C. in ice/water bath. $HBr_{(g)}$ was bubbled through the DMC solution for about 30 min. The reaction was controlled by monitoring by TLC the disappearance of the starting sugar (ether/hexane 1:9 v/v). When the reaction was complete the solvent was evaporated at a temperature not higher that 20° C. and kept for 20 min in deep vacuum to remove the traces of HBr. A solution of Na-salt of the base was fast filtrated and the filtrate was added to the sugar component. The reaction was kept overnight at ambient temperature, neutralized with 0.1 N $H_2SO_4$ and evaporated. The residue was distributed between 700 mL of ethyl acetate and 700 mL of water. The organic fraction was washed with water (150 mL), brine (150 mL), dried over $Na_2SO_4$ and evaporated to give a semi crystalline mixture. Toluene (500 mL) was added to form a light tan precipitate of nonreacted heterocyclic base 2.5 g (25%). The filtrate was concentrated up to the volume of 50 mL and loaded on the glass filter with silica gel (10×10 cm). The filter was washed with 10% ethyl acetate in toluene collecting 500 mL fractions. Fraction 2–4 contained the title compound; fractions 6–7 contained the heterocyclic base.

Fractions 2–4 were evaporated, ether was added to the colorless oil and the mixture was sonicated for 5 min. The off-white precipitate was formed, yield 7.4 g (50%), mother liquid was evaporated and the described procedure was repeated to yield 0.7 g more of the title nucleoside. Total yield is 8.1 g (54.4%).

$T_m$ 67–70° C.
$^1$H-NMR (DMSO-d6): 8.66 (s, 1H, H-2), 8.07 (s, 1H, H-8), 7.62–7.34 (m, 6H, dichlorophenyl), 6.22 (s, 1H, H-1'), 5.64 (s, 1H, H-3'), 4.78–4.55 (m, 4H, $CH_2$-benzyl, 2'-OH, H-4'), 4.20 (s, 2H, $CH_2$-benzyl), 3.97–3.93 and 3.78–3.75 (dd, 1H, H-5'), 0.92 (s, 3H, 2'-methyl)
MS: 743.99 (M+H);
Recovered base (total): 4 g as off-white crystals,
$T_m$ 228–230° C.

Step 3. 7-(2'-methyl-β-D-ribofuranosyl)-4-chloro-5-iodo-pyrrolo[2,3-d]pyrimidine To the solution of the compound from the previous step (8 g, 10.7 mmol) in DCM (200 mL) at −78° C. was added boron trichloride (1M in DCM, 88 mL, 88 mmol) dropwise. The mixture was stirred at −78° C. for 2.5 hours and additionally overnight at −20° C. The reaction was quenched by addition of methanol/DCM (90 mL, 1:1) and the resulting mixture stirred at −20° C. for 30 min, then neutralized by aqueous ammonia at the same temperature. The solid was filtered and washed with methanol/DCM (250 mL, 1:1). The filtrates were combined with 50 mL of silica gel and evaporated up to dryness. Dry silica was loaded on the glass filter with silica gel (10×10 cm). The filter was washed with ethyl acetate collecting 500 mL fractions. Fraction 2–4 contained the title compound. The solvent was evaporated and the residue crystallized from acetone/hexane to give 3.3 g (72%) of title nucleoside.

$^1$H-NMR (DMSO-d6): 8.84 (s, 1H, H-2), 8.20 (s, 1H, H-8), 6.21 (s, 1H, H-1'), 4.00–3.60 (m, sugar), 0.84 (s, 3H, 2'-methyl);

MS: 426.26 (M+H);

$T_m$ 182–185° C.

Step 4. 7-(2'-methyl-β-D-ribofuranosyl)-4-amino-5-iodo-pyrrolo[2,3-d]pyrimidine

Nucleoside (1.5 g, 3.5 mmol) prepared above was treated with liquid ammonia at 85° C. for 24 hours in the metal pressure reactor. After evaporation of ammonia the residue was dissolved in methanol and co-evaporated with silica gel (about 20 mL). Silica gel bearing the product was on the column (5×10 cm) with silica gel in acetone collecting 50 mL fractions. Fractions 2–8 contained the titled compound. Acetone was evaporated and the residue crystallized from methanol/acetonitrile to give 1.2 g (84%) of the titled nucleoside $T_m$ 220–222° C. (dec)

$^1$H-NMR (DMSO-d6): 8.20 (s, 1H, H-2), 7.80 (s, 1H, H-8), 6.80–6.50 (bs, 1H, NH2), 6.09 (s, 1H, H-1'), 5.19 (t, 1H, sugar), 5.13–5.11 (m, 2H, sugar), 4.00–3.70 (m, 3H, sugar), 3.60–3.20 (m, 1H, sugar), 0.84 (s, 3H, 2'-methyl);

MS 407.32 (M+H).

Step 5. 7-(2'-methyl-β-D-ribofuranosyl)-4-amino-5-(trimethylsilanylethyn-1-yl)-pyrrolo[2,3-d]pyrimidine Aminonucleoside synthesized in previous step (1.7 g, 4.2 mmol) was dissolved in the mixture of 12 mL of dry DMF and 28 mL of dry THF. Triethylamine (3.6 mmol, 0.5 mL), CuI (1 mmol, 80 mg) were added and the flask was filled with argon. Tetrakis(triphenylphosphine)palladium(0) (0.04 mmol, 46 mg) followed with (trimethylsilyl)acetylene was added and the mixture was stirred under argon for 20 hours.

The solvent was evaporated and the residue in acetone was filtered through a silica gel (5×10 cm). Acetone was evaporated, residue was dissolved in actonitrile and filtered again through the silica gel column of the same size, and elution was made with pure acetonitrile. Acetonitrile was concentrated up to small volume, about 10 volumes of ether was added and the solution was sonicated for 5 min. White crystals of the titled compound were formed, yield 0.8 g (71%).

$T_m$ 188–191° C. (dec);

$^1$H-NMR (DMSO-d6): 8.17 (s, 1H, H-2), 7.92 (s, 1H, H-8), 7.20–6.80 (t, 1.2H, NH2), 5.83 (s, 1H, H-1'), 3.75–3.20 (m, sugar), 0.45 (s, 3H, 2'-methyl), 0 (s, 9H, Si(CH3)3).

Step 6. Preparation of Title Compound

Silylated nucleoside (1 g, 2.6 mmol) was dissolved in 10 mL of methanol, 10 mL of NH$_4$OH was added and the mixture left at ambient temperature for 1 hour. Solvent was evaporated, the residue dissolved in methanol and co-evaporated with silica gel (30 mL). Dry silica was loaded on the glass filter with silica gel (4×6 cm), and the compound was eluted with acetone. The solvent was evaporated and the residue crystallized from methanol/acetonitrile, yield 0.5 g (62%).

$T_m$ 209–219° C. (dec)

Comparative Example A

Preparation of 7-(2'-C-methyl-β-D-ribofuranosyl)-4-amino-5-(propyn-1-yl)-pyrrolo[2,3-d]pyrimidine

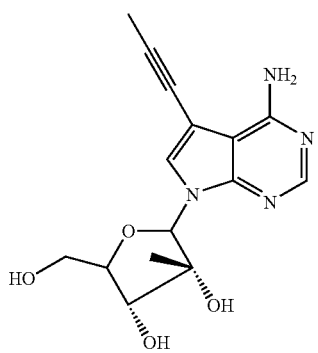

To a solution of the product from Step 4, Example 2 (50.0 mg, 0.123 mmol) in 3.2 mL THF-DMF (2:1 v/v) was added CuI (9.2 mg, 0.048 mmol), TEA (16 μl, 0.113 mmol), tetrakis(triphenylphosphine)palladium(0) (14.0 mg, 0.012 mmol) and the solution degassed with argon. The solution was cooled to 0° C. and propyne gas was bubbled through the solution for 1 min. The reaction was then allowed to slowly warm to room temperature over 4 hours. The procedure of charging reaction with propyne was repeated twice more until no traces of starting material was observed by TLC. The reaction mixture was concentrated in vacuo, taken up in DMF and purified by RP HPLC on Phenominex column (250×20 mm) using gradient of acetonitrile in water from 0 to 50% over 30 min at 10 mL/min to yield 26 mg (66%) of the title compound.

$^1$H-NMR (CD$_3$OD): 8.07 (s, 1H), 7.67 (s, 1H), 6.19 (s, 1H), 4.11–3.84 (m, 4H, sugar), 2.09 (s, 3H), 0.82 (s, 3H).

MS 319.11 (M+H).

Comparative Example B

Preparation of 7-(2'-C-methyl-β-D-ribofuranosyl)-4-amino-5-(butyn-1-yl)-pyrrolo[2,3-d]pyrimidine

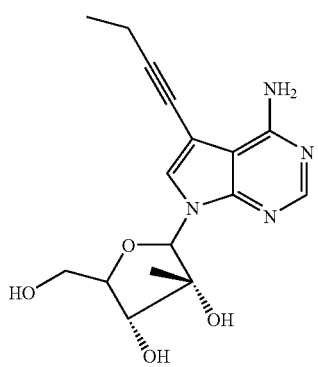

To a solution of the product from Step 4, Example 2 (50.0 mg, 0.123 mmol) in 3.2 mL THF-DMF (2:1 v/v) was added CuI (9.2 mg, 0.048 mmol), TEA (16 μl, 0.113 mmol), tetrakis(triphenylphosphine)palladium(0) (14.0 mg, 0.012 mmol) and the solution degassed with argon. The solution was cooled to 0° C. and butyne gas was bubbled through the solution for 1 min. The reaction was then allowed to slowly warm to room temperature over 4 hours. The reaction mixture was concentrated in vacuo, taken up in DMF and purified by RP HPLC on Phenominex column (250×20 mm) using gradient of acetonitrile in water from 0 to 50% over 30 min at 10 mL/min to yield 13 mg (32%) of the title compound.

$^1$H-NMR (CD$_3$OD): 8.08 (s, 1H), 7.67 (s, 1H), 6.19 (s, 1H), 4.11–3.80 (m, 4H, sugar), 2.48 (s, 3H), 1.26 (t, 3H). 0.83 (s, 3H).

MS 333.13 (M+H).

Comparative Example C

Preparation of 7-(2'-C-methyl-β-D-ribofuranosyl)-4-amino-5-(3-hydroxypropyn-1-yl)-pyrrolo[2,3-d]pyrimidine

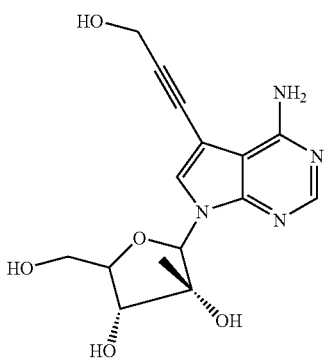

A solution was made of the product from Step 4, Example 2 (50.0 mg, 0.1231 mmol) in 5 ml dimethylformamide. The solution was degassed by bubbling with argon while sonicating for 5 min. To this solution was added triethylamine (16.0 μl, 0.1145 mmol), copper iodide (9.4 mg, 0.0492 mmol), and tetrakis(triphenyl-phosphine)palladium(0) (14.2 mg, 0.0123 mmol). Next, propargyloxytrimethylsilane (113.7 μl, 0.7386 mmol) was added. The mixture was stirred under argon for 4 hours. Upon completion, the mixture was concentrated in vacuo. The reaction crude was dissolved in 1 mL dimethylformamide, diluted to 50 mL with deionized water and then washed through a celite pad. The solution was again concentrated down to dryness, then redissolved in 1.0 ml dimethylformamide and 3.5 ml water. Purification was via HPLC.

$^1$H-NMR (CD$_3$OD): 8.10 (s, 1H), 7.80 (s, 1H), 6.21 (s, 1H), 4.44 (d, 2H), 4.11–3.82 (m, 4H), 0.83 (s, 3H). MS: 335.13 (m/z).

Comparative Example D

Preparation of 7-(2'-C-methyl-β-D-ribofuranosyl)-4-amino-5-(3-aminopropyn-1-yl)-pyrrolo[2,3-d]pyrimidine

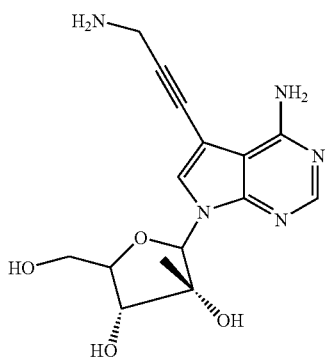

Step 1. Prop-2-ynyl-carbamic acid 9H-fluoren-9-ylmethyl ester

A solution was made of propargylamine (250 μl, 3.645 mmol) in diisopropylethylamine (1.273 ml, 7.290 mmol). Next, 9-fluorenylmethyl chloroformate was dissolved in 7 ml dimethylformamide and added to the reaction mixture. The mixture was stirred under argon overnight at room temperature. After completion, the solution was reduced in vacuo. An ethyl acetate/water extraction procedure was performed to isolate the product.

MS: 278.10 (m/z).

Step 2. 7-(2'-C-methyl-β-D-ribofuranosyl)-4-amino-5-(3-aminopropyn-1-yl)-pyrrolo[2,3-d]pyrimidine A solution was made of the product from Step 4, Example 2 (124.5 mg, 0.3065 mmol) in 10 ml dimethylformamide. The solution was degassed by bubbling with argon while sonicating for 5 min. To this solution was added triethylamine (39.7 μl, 0.2850 mmol), copper iodide (23.5 mg, 0.1226 mmol), and tetrakis(triphenylphosphine)palladium (0) (35.4 mg, 0.0307 mmol). Next, fmoc-propargylamine from Step 1 (465.9 mg, 0.1.680 mmol) was added. The mixture was stirred under argon for 4 hours. Upon completion, the mixture was concentrated in vacuo. The reaction crude was dissolved in 1 mL dimethylformamide, and then diluted to 50 mL with deionized water and then washed through a celite pad. The solution was again concentrated down to dryness, then redissolved in 1.0 ml dimethylformamide and 3.5 ml water. Purification was via HPLC.

$^1$H-NMR (DMF-d$_7$): 8.17 (s, 1H), 8.08 (s, 1H), 6.28 (s, 1H), 5.80–5.32 (m, 3H), 4.19–3.82 (m, 4H), 3.37–3.30 (m, 2H), 0.83 (s, 3H). MS: 334.15 (m/z).

Example 3

Preparation of 7-(2'-C-methyl-β-D-ribofuranosyl)-4-amino-5-(2-phenylethyl-1yl)-pyrrolo[2,3-d]pyrimidine

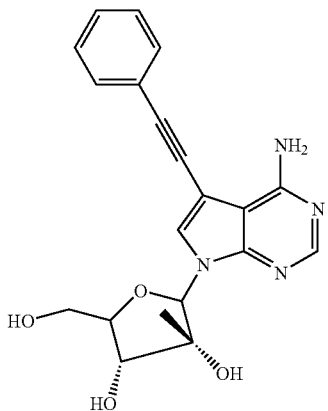

A solution was made of the product from Step 4, Example 2 (50.0 mg, 0.1231 mmol) in 5 ml dimethylformamide. The solution was degassed by bubbling with argon while sonicating for 5 min. To this solution was added triethylamine (16.0 μl, 0.1145 mmol), copper iodide (9.4 mg, 0.0492 mmol), and tetrakis(triphenylphosphine)palladium(0) (14.2 mg, 0.0123 mmol). Next, phenylacetylene (81.1 μl, 0.7386 mmol) was added. The mixture was stirred under argon for 4 hours. Upon completion, the mixture was concentrated in vacuo. The reaction crude was dissolved in 1 mL dimethylformamide, diluted to 50 mL with deionized water and then washed through a celite pad. The solution was again concentrated down to dryness, then redissolved in 1.0 ml dimethylformamide and 3.5 ml water. Purification was via HPLC.

$^1$H-NMR (CD$_3$OD): 8.14 (s, 1H), 7.91 (s, 1H), 7.54–7.51 (m, 2H), 7.40–7.36 (m, 3H), 6.25 (s, 1H), 4.16-3.85 (m, 4H), 0.87 (s, 3H). MS: 381.14 (m/z).

Example 4

Preparation of 7-(2'-C-methyl-β-D-ribofuranosyl)-4-amino-5-(ethyl 2-carboxylethyn-1yl)-pyrrolo[2,3-d]pyrimidine

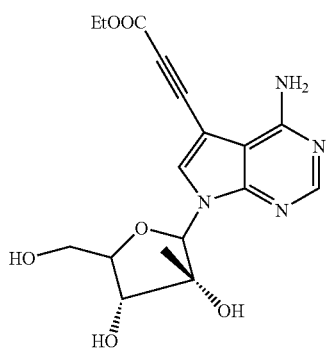

To a solution of the product from Step 4, Example 2 (450.0 mg, 1.108 mmol) in 28.8 mL THF-DMF (2:1 v/v) was added CuI (0.082 g, 0.432 mmol), TEA (144 μl, 1.035 mmol), tetrakis(triphenylphosphine)palladium(0) (0.126 g, 0.108 mmol) and the solution degassed with argon. Ethyl propiolate (100 μl, 1.011 mmol) was added and the reaction was heated to 55° C. An additional 100 μl of ethyl propiolate was added every hour for six hours until no starting material was present by TLC. The reaction mixture was concentrated in vacuo, taken up in DMF and purified by RP HPLC on PHenominex column (250×20 mm) using gradient of acetonitrile in water from 0 to 60% over 30 min at 10 mL/min to yield 115 mg (28%) of the title compound.

$^1$H-NMR (CD3OD): 8.24 (s, 1H), 8.17 (s, 1H), 6.24 (s, 1H), 4.28 (q, 2H), 4.13–3.87 (m, 4H, sugar), 1.34 (t, 3H), 0.86 (s, 3H).

MS 377.11 (M+H).

Example 5

Preparation of 7-(2'-C-methyl-β-D-ribofuranosyl)-4-amino-5-(2-carboxylethyn-1yl)-pyrrolo[2,3-d]pyrimidine

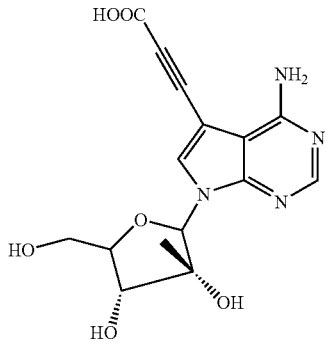

To the product from Example 4 (20.0 mg, 0.053 mmol) was added 500 μl of 1N NaOH and stirred at room temperature for 30 min. The reaction was then diluted with water and purified by RP HPLC on PHenominex column (250×20 mm) using gradient of acetonitrile in water from 0 to 60% over 30 min at 10 mL/min to yield 7.0 mg (38%) of the title compound.

$^1$H-NMR (CD3OD): 8.10 (s, 1H), 7.96 (s, 1H), 6.22 (s, 1H), 4.12–3.82 (m, 4H, sugar), 0.84 (s, 3H).

MS 349.10 (M+H).

Example 6

Preparation of 7-(2'-C-methyl-β-D-ribofuranosyl)-4-amino-5-(2-cis-methoxyethen-1-yl-pyrrolo[2,3-d]pyrimidine

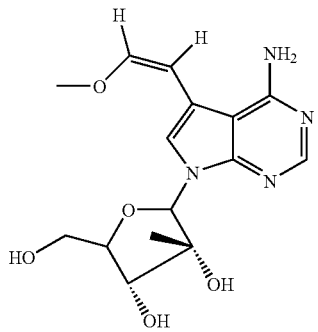

Step 1: Preparation of 7-(2'-C-methyl-β-D-ribofuranosyl)-4-amino-5-(formyl)-pyrrolo[2,3-d]pyrimidine 7-(2'-C-methyl-β-D-ribofuranosyl)-4-amino-5-(formyl)-pyrrolo[2,3-d]pyrimidine was synthesized according to the procedure described by Shin-ichi Watanabe and Tohru Ueda in Nucleosides and Nucleotides (1983) 2(2), 113–125. In the synthesis of the title compound however, 7-(2'-C-methyl-β-D-ribofuranosyl)-4-amino-pyrrolo[2,3-d]pyrimidine (See Carroll, et al.,[11,12]) was substituted in place of tubercidin.

$H^1$-NMR (CD$_3$OD): 0.9 (s, 3H, 2'-CH$_3$), 3.8–4.2 (m, 4H, sugar), 6.3 (s, 1H, 1'-H), 8.2 and 8.6 (s, 1H, —Ar), 9.7 (s, 1H, -aldehyde-H). MS: 309.13 (M+H).

Step 2: Preparation of the Title Compound

The product from Step 1 above (0.050 g, 0.162 mmol) was dissolved in 2 mL DMSO and added dropwise to the preformed ylide of (methoxymethyl)-triphenylphosphonium chloride and stirred at room temperature. The ylide was formed by dissolving (0.555 g, 1.62 mmol) (methoxymethyl)triphenylphosphonium chloride in 10 mL DMSO and adding 0.81 mL 2 M methylsulfinyl carbanion solution (1.62 mmol) and stirred at room temperature for 15 min. After stirring at room temperature for 4 hours, a second charge of (1.62 mmol) of the ylide of (methoxy-methyl)triphenylphosphonium chloride was added to the reaction and the reaction was allowed to stir at room temperature overnight. The reaction was quenched with water and diluted with methylene chloride. The layers were separated and the organic layer was extracted with water twice. The aqueous layers were combined and concentrated in vacuo and purified by RP HPLC on Phenominex column (250×20 mm) using gradient of acetonitrile in water from 0 to 30% over 30 min at 10 mL/min to yield 20 mg of the trans enol ether and 10 mg of cis isomer, (56%) yield.

(cis-isomer) $H^1$-NMR (CD$_3$OD): 0.82 (s, 3H, 2'-CH$_3$), 3.8 (s, 3H, —OCH$_3$) 3.8–4.2 (m, 4H, sugar), 5.56 (d, 1H), 6.23 (s, 1H, 1'-H), 6.25 (d, 1H), 7.8 and 8.0 (s, 1H, —Ar).

Example 7

Preparation of 7-(2'-C-methyl-β-D-ribofuranosyl)-4-amino-5-(ethen-1-yl)-pyrrolo[2,3-d]pyrimidine

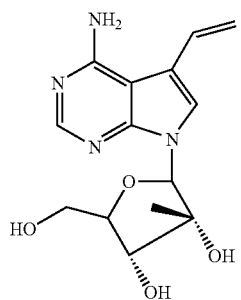

The title compound from Example 2 (0.040 g, 0.0132 mmol) was dissolved in 3 mL THF and 22 mg of Lindlar's catalyst was added. The solution was stirred at ambient temperature under 1 atm of hydrogen (via balloon) for 7 days. The balloon was recharged with hydrogen at the beginning of each day. After 7 days, the reaction was filtered through celite to remove catalyst, concentrated in vacuo, and purified by reverse phase HPLC on Phenominex column (250×20 mm) using a gradient of acetonitrile in water from 0 to 30% over 30 min at 10 mL/min to yield 30 mg (75% yield) of the title compound.

H1-NMR (CD$_3$OD): 0.835 (s, 3H, 2'-CH$_3$), 3.8–4.2 (m, 4H, sugar), 5.2 (dd, 1H), 5.5 (dd, 1H), 6.23 (s, 1H, 1'-H), 6.9 ((dd, 1H), 7.73 and 8.06 (s, 1H, —Ar). MS: 307.15 (M+H).

Example 8

General Preparation of Nucleoside Triphosphates

An appropriately substituted 7-(β-D-ribofuranosyl)-pyrrolo[2,3-d]pyrimidine (0.1 mmol) was co-evaporated 3 times with dry DMF, dissolved in 2 mL of PO(OMe)$_3$, cool to 5° C. and POCl$_3$ (35 μL) and proton sponge (64 mg) were added. The mixture was stirred at 5° C. for 3 h, then tetrabutylammonium pyrophosphate (2 mmol, 4 mL of 0.5M solution in DMF) was added and the mixture was kept for 2 more h at the same temperature. The reaction was quenched with (Et$_3$N)HCO$_3$ buffer (pH 7.5) followed with water. The solvents were evaporated, the residue dissolved in methanol (3 mL) and precipitated with ether (30 mL). The solid residue was purified by IE HPLC on Vidac column (250×10 mm) 0 to 100% B. Buffer A was 25 mM NaH$_2$PO$_4$/Na$_2$HPO$_4$, pH 3, buffer B was 310 mM NaH$_2$PO$_4$/Na$_2$HPO$_4$, pH 3. The last peak was collected, concentrated up to the volume of 5 mL and repurified on RP HPLC on Phenominex column (250×20 mm) in gradient from 0 to 100% of buffer B in buffer A. Buffer A was 0.5 M aqueous solution of triethylammonium acetate, buffer B was 0.5 M acetonitrile solution of triethylammonium acetate. Fractions containing the title compound were combined, evaporated, co-evaporated 3 times with water and lyophilized from water.

Further transformations may be made on the deazapurine ring to obtain the desired final compound.

Example 9

General Preparation of Nucleoside Monophosphate

An appropriately substituted 7-(β-D-ribofuranosyl)-pyrrolo[2,3-d]pyrimidine (0.1 mmol) was co-evaporated 3 times with dry DMF, dissolved in 2 mL of PO(OMe)$_3$, cool to 5° C. and POCl$_3$ (35 μL) and proton sponge (64 mg) were added. The mixture was stirred at 5° C. for 3 h. The reaction was quenched with (Et$_3$N)HCO$_3$ buffer (pH 7.5) followed with water. The solvents were evaporated, the residue dissolved in methanol (3 mL) and precipitated with ether (30 mL). The solid residue was purified by IE HPLC on Vidac column (250×10 mm) 0 to 100% B. Buffer A was 25 mM NaH$_2$PO$_4$/Na$_2$HPO$_4$, pH 3, buffer B was 310 mM NaH$_2$PO$_4$/Na$_2$HPO$_4$, pH 3. The last peak was collected, concentrated up to the volume of 5 mL and repurified on RP HPLC on Phenominex column (250×20 mm) in gradient from 0 to 100% of buffer B in buffer A. Buffer A was 0.5 M aqueous solution of triethylammonium acetate, buffer B was 0.5 M acetonitrile solution of triethylammonium acetate. Fractions containing the title compound were combined, evaporated, co-evaporated 3 times with water and lyophilized from water.

Further transformations may be made on the deazapurine ring to obtain the desired final compound.

Biological Examples

Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al. *Jnl. of Vir.*, 73:1649–1654, 1999; Ishii et al., *Hepatology*, 29:1227–1235, 1999; Lohmann et al., *Jnl of Bio. Chem.*, 274:10807–10815, 1999; and Yamashita et al., *Jnl. of Bio. Chem.*, 273:15479–15486, 1998.

WO 97/12033, filed on Sep. 27, 1996, by Emory University, listing C. Hagedom and A. Reinoldus as inventors, which claims priority to U.S. Provisional Patent Application Ser. No. 60/004,383, filed on September 1995, describes an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996:1 (Supp 4) 18–24.

Screens that measure reductions in kinase activity from HCV drugs are disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs are disclosed in U.S. Pat. No. 5,861,267 to Su et al., U.S. Pat. No. 5,739,002 to De Francesco et al., and U.S. Pat. No. 5,597,691 to Houghton et al.

Example 2

Replicon Assay

A cell line, ET (Huh-lucubineo-ET) is used for screening of compounds of the present invention for HCV RNA dependent RNA polymerase. The ET cell line is stably transfected with RNA transcripts harboring a $I_{389}$luc-ubineo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells are grown in DMEM, supplemented with 10% fetal calf serum, 2 mM Glutamine, Penicillin (100 IU/mL)/Streptomycin (100 µg/mL), 1× nonessential amino acids, and 250 µg/mL G418 ("Geneticin"). They are all available through Life Technologies (Bethesda, Md.). The cells are plated at $0.5–1.0×10^4$ cells/well in the 96 well plates and incubated for 24 hrs before adding nucleoside analogs. Then the compounds each at 5 and 50 µM will be added to the cells. Luciferase activity will be measured 48–72 hours later by adding a lysis buffer and the substrate (Catalog number Glo-lysis buffer E2661 and Bright-Glo leuciferase system E2620 Promega, Madison, Wis.). Cells should not be too confluent during the assay. Percent inhibition of replication will be plotted relative to no compound control. Under the same condition, cytotoxicity of the compounds will be determined using cell proliferation reagent, WST-1 (Roche, Germany). The compounds showing antiviral activities, but no significant cytotoxicities will be chosen to determine $IC_{50}$ and $TC_{50}$.

Example 3

Cloning and Expression of Recombinant HCV-NS5b

The coding sequence of NS5b protein is cloned by PCR from pFKI$_{389}$luc/NS3-3'/ET as described by Lohmann, V., et al. (1999) *Science* 285, 110–113 using the following primers:

aggacatggatccgcggggtcgggcacgagacag (SEQ. ID. NO. 1)

aaggctggcatgcactcaatgtcctacacatggac (SEQ. ID. NO. 2)

The cloned fragment is missing the C terminus 21 amino acid residues. The cloned fragment is inserted into an IPTG-inducible expression plasmid that provides an epitope tag (His)6 at the carboxy terminus of the protein.

The recombinant enzyme is expressed in XL-1 cells and after induction of expression, the protein is purified using affinity chromatography on a nickel-NTA column. Storage condition is 10 mM Tris-HCl pH 7.5, 50 mM NaCl, 0.1 mM EDTA, 1 mM DTT, 20% glycerol at −20° C.

Example 4

HCV-NS5b Enzyme Assay

The polymerase activity is assayed by measuring incorporation of radiolabeled UTP into a RNA product using a biotinylated, heteropolymeric template, which includes a portion of the HCV genome. Typically, the assay mixture (50 µL) contains 10 mM Tris-HCl (pH 7.5), 5 mM MgCl$_2$, 0.2 mM EDTA, 10 mM KCl, 1 unit/µL RNAsin, 1 mM DTT, 10 µM each of NTP, including [$^3$H]-UTP, and 10 ng/µL heteropolymeric template. Test compounds are initially dissolved in 100% DMSO and further diluted in aqueous buffer containing 5% DMSO. Typically, compounds are tested at concentrations between 1 nM and 100 µM. Reactions are started with addition of enzyme and allowed to continue at 37° C. for 2 hours. Reactions are quenched with 8 µL of 100 mM EDTA and reaction mixtures (30 µL) are transferred to streptavidin-coated scintillation proximity microtiter plates (FlashPlates) and incubated at 4° C. overnight. Incorporation of radioactivity is determined by scintillation counting.

Anti-HCV Activity Results

Each of the compounds of this invention which were tested for an $IC_{50}$ exhibited an $IC_{50}$ value of less than 12.5 µM whereas each of comparative examples A–D exhibited an $IC_{50}$ value of greater than 50 µM.

Furthermore, insertion of a methyl group on the 4-amino moiety of a compound of this invention to provide for the corresponding methylamino substituent (CH₃NH—) resulted in a significant reduction in the $IC_{50}$ value for the Replicon Assay of Example 2 above.

Formulation Examples

The following are representative pharmaceutical formulations containing a compound of the present invention.

Example 1

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Example 4

Injectable Formulation

The following ingredients are mixed to form an injectable formulation.

| Ingredient | Amount |
| --- | --- |
| compound of this invention | 0.2 mg–20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
| --- | --- |
| compound of the invention | 500 mg |
| Witepsol ® H-15 | balance |

What is claimed is:

1. A compound of formula Ia:

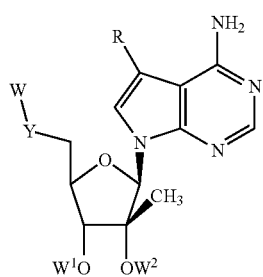

wherein
- Y is selected from the group consisting of a bond, —CH$_2$— or —O—;
- each of W, W$^1$ and W$^2$ is independently selected from the group consisting of hydrogen, acyl, oxyacyl, phosphonate, phosphate, phosphate esters, phosphonamidate, phosphorodiamidate, phosphoramidate monoester, cyclic phosphoramidate, cyclic phosphorodiamidate, phosphoramidate diester, and —C(O)CHR$^3$ NH$_2$, where R$^3$ is a sidechain of an amino acid, or where W and W$^1$ may optionally join together to form a cyclic phosphonamidate;
- R is —CH=CH-Q$^2$; and
- Q$^2$ is selected from hydrogen or cis-methoxy;

or pharmaceutically acceptable salts or partial salts thereof, wherein
- substituted alkyl refers to an alkenyl group having from 1 to 3 substituents selected from the group consisting of alkoxy, substituted alkoxy, acyl, acylamino, acyloxy, oxyacyl, amino, substituted amino, aminoacyl, anryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
- alkoxy refers to alkyl-O—;
- substituted alkoxy refers to (substituted alkyl)-O—;
- acyl refers to a moiety selected from the group consisting of H—C(O)—, alkyl-C(O)—, substituted alkyl-C(O)—, alkenyl-C(O)—, substituted alkynyl-C(O)—, alkynyl-C(O)—, substituted alkynyl-C(O)—, cycloalkyl-C(O)—, substituted cycloalkyl-C(O)—, aryl-C(O)—, substituted aryl-(O)—, heteroaryl-C(O)—, substituted heteroaryl-C(O), hetercylyclyl-C(O)—, and substituted heterocyclyl-C(O)—;
- acylamino refers to —C(O)NR$^4$R$^4$ where each R$^4$ independently is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R$^4$ is joined to form together with the nitrogen atom a heterocyclyl or substituted heterocyclyl ring;
- acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—heterocyclyl-C(O)O—, and substituted heterocyclyl-C(O)O—;
- oxyacyl refers to a moiety selected from the group consisting of alkyl-OC(O)—, substituted alkyl-OC(O)—, alkenyl-OC(O)—, substituted alkenyl-OC(O)—, alkynyl-OC(O)—, substituted alkynyl—OC(O)—, aryl—OC(O)—, substituted aryl—OC(O)—, cycloalkyl—OC(O)—, substituted cycloalkyl-OC(O)—, heteroaryl-OC(O)—, substituted heteroaryl-OC(O)—, heterocyclyl—OC(O)—, and substituted heterocyclyl-OC(O)—;
- substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted and, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proviso that any hydroxyl substitution is not attached to an unsaturated carbon atom;
- substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl heterocyclyl, and substituted heterocyclyl
- amino refers to —NH$_2$;
- substituted amino refers to —NR'R" where R' and R" independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroayl, substituted heteroaryl, heterocyclyl, substituted heterocyclyl and where R' and R" are joined, together with the nitrogen bound thereto to form a heterocyclyl or substituted heterocyclyl ring provided that R' and R" are both not hydrogen;

aminoacyl refers to a moiety selected from the group consisting of —$NR^5C(O)$alkyl, —$NR^5C(O)$substituted alkyl, —$NR^5C(O)$cycloalkyl, —$NR^5C(O)$substituted cycloalkyl, —$NR^5C(O)$alkenyl, —$NR^5C(O)$substituted alkenyl, —$NR^5C(O)$alkynyl, —$NR^5C(O)$substituted alkynyl, —$NR^5C(O)$aryl, —$NR^5C(O)$substituted aryl, —$NR^5C(O)$heteroaryl, —$NR^5C(O)$ substituted heteroaryl, —$NR^5C(C)$heterocyclyl, and —$NR^5C(O)$ substituted heterocyclyl where $R^5$ is hydrogen or alkyl;

aryl refers to a monovalent aromatic carbocyclic group of from 6 to 14 carbon atoms having a single ring or multiple condensed rings which condensed rings may or may not be aromatic provided that the point of attachment is at an aromatic carbon atom; substituted aryl refers to an aryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

aryloxy refers to aryl-O—;

substituted aryloxy refers to (substituted aryl)-O—;

carboxyl refers to —COOH or salts thereof;

carboxyl ester refers to a moiety selected from the group consisting of —C(O)O-alkyl, —C(O)O- substituted alkyl, —C(O)Oaryl, and —C(O)O-substituted aryl;

cycloalkyl refers to a cyclic alkyl group of from 3 to 10 carbon atoms having single or multiple cyclic rings;

substituted cycloalkyl refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

cycloalkoxy refers to —O-cycloalkyl;

substituted cycloalkoxy refers to —O-(substituted cycloalkyl);

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur, —S(O)— and —$SO_2$— within the ring, wherein the heteroaryl group can have a single ring or multiple condensed rings wherein the condensed rings may or may not be aromatic and/or contain a heteroatom provided that the point of attachment is through an aromatic ring atom;

substituted heteroaryl refers to a heteroaryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated group having a single ring or multiple condensed rings, from 1 to 10 carbon atoms and from 1 to 4 hetero atoms selected from the group consisting of nitrogen, oxygen, sulfur, —S(O)—, and —$S(O)_2$— within the ring wherein, in fused ring systems, one or more the rings can be cycloalkyl, aryl or heteroaryl provided that the point of attachment is through the heterocyclyl ring;

substituted heterocyclyl refers to a heterocyclyl group substituted with from 1 to 3 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl substituted heterocyclyloxy refers to —O-(substituted heterocyclyl);

phosphate refers to a moiety selected from the group consisting of —$OP(O)(OH)_2$, (monophosphate or phospho), —$OP(O)(OH)OP(O)(OH)_2$ (diphosphate or diphospho) and —$OP(O)(OH)OP(O)(OH)OP(O)(OH)_2$ (triphosphate or triphospho) and salts thereof, including partial salts thereof;

phosphate ester refers to a mono-, di- and tri-phosphate group, wherein one or more of the hydroxyl groups is replaced by an alkoxy group;

phosphonate refers to a moiety selected from the group consisting of —$OP(O)(R^6)(OH)$ and —$OP(O)(R^6)(OR^6)$ and salts thereof, including partial salts thereof, wherein each $R^6$ is independently selected from hydrogen, alkyl, substituted alkyl, carboxyl, and carboxyl ester;

phosphorodiamidate refers to

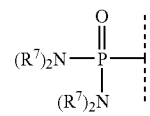

where each $R^7$ may be the same or different and each is hydrogen, alkyl, substituted alkyl, cycloalkyl, or substituted cycloalkyl;

phosphoramidate monoester refers to

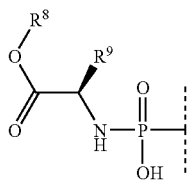

where $R^8$ is hydrogen or alkyl and $R^9$ may be the same or different and each is hydrogen, alkyl, substituted alkyl, cycloalkyl, or substituted cycloalkyl;
phosphoramidate diester refers to

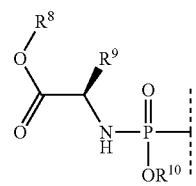

where $R^8$ is hydrogen or alkyl, $R^{10}$ is aryl, substituted aryl, alkyl, or substutituted alkyl, and each $R^9$ is hydrogen, alkyl, substituted alkyl, cycloalkyl, and substituted cycloalkyl;
cyclic phosphoramidate refers to

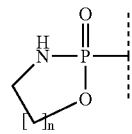

where n is 1 to 3;
cyclic phosphorodiamidate refers to

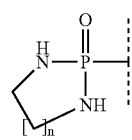

where n is 1 to 3;
phosphonamidate refers to

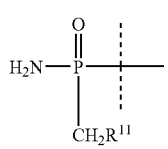

where $R^{11}$ is hydrogen, alkyl, substituted alkyl, cycloalkyl, or substituted cycloalkyl;
thiol refers to —SH,
thioalkyl refers to —S-alkyl;
substituted thioalkyl refers to —S-(substituted alkyl);
thiocycloalkyl refers to —S-cycloalkyl;
substituted thiocycloalkyl refers to —S-(substituted cycloalkyl);
thioaryl refers to —S-aryl;
substituted thioaryl refers to —S-(substituted aryl);
thioheteroaryl refers to —S-heteroaryl;
substituted thioheteroaryl refers to —S-(substituted heteroaryl);
thioheterocyclyl refers to —S-heterocyclyl; and
substituted thioheterocyclyl refers to —S-(substituted heterocyclyl).

2. A compound selected from the group consisting of:
7-(2'-C-methyl-β-D-ribofuranosyl)-4-amino-5-(ethen-1-yl)-pyrrolo[2,3-d]pyrimidine;
7-(2'-C-methyl-β-D-ribofuranosyl)-4-amino-5-(2-cis-methoxy-ethen-1-yl)-pyrrolo[2,3-d]pyrimidine;
7-(2'-C-methyl-5'-monophospho-β-D-ribofuranosyl)-4-amino-5-(ethen-1-yl)-pyrrolo[2,3-d]pyrimidine;
7-(2'-C-methyl-5'-diphospho-β-D-ribofuranosyl)-4-amino-5-(ethen-1-yl)-pyrrolo[2,3-d]pyrimidine;
7-(2'-C-methyl-5'-triphospho-β-D-ribofuranosyl)-4-amino-5-(ethen-1-yl)-pyrrolo[2,3-d]pyrimidine;
7-(2'-C-methyl-5'-monophospho-β-D-ribofuranosyl)-4-amino-5-(2-cis-methoxy-ethen-1-yl)-pyrrolo[2,3-d]pyrimidine;
7-(2'-C-methyl-5'-diphospho-β-D-ribofuranosyl)-4-amino-5-(2-cis-methoxy-ethen-1-yl)-pyrrolo[2,3-d]pyrimidine; and
7-(2'-C-methyl-5'-triphospho-β-D-ribofuranosyl)-4-amino-5-(2-cis-methoxy-ethen-1-yl)-pyrrolo[2,3-d]pyrimidine;
or pharmaceutically acceptable salts or partial salts thereof.

3. A pharmaceutical composition comprising a pharmaceutically acceptable diluent and a therapeutically effective amount of a compound according to any one of claims 1 to and 2.

4. A method for treating hepatitis C virus (HCV) in a mammalian patient suffering from HCV which method comprises administering to said mammal a pharmaceutical composition according to claim 3.

5. A compound of formula II:

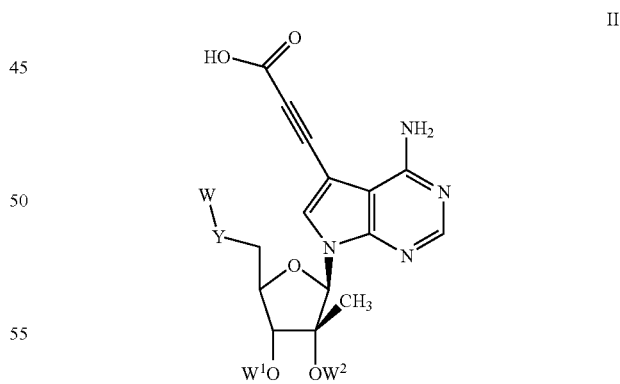

wherein
Y is selected from the group consisting of a bond, —CH$_2$— or —O—;
each of W, $W^1$ and $W^2$ is independently selected from the group consisting of hydrogen, acyl, oxyacyl, phosphonate, phosphate esters, phosphate, phospho, diphospho, triphospho, phosphonamidate, phosphorodiamidate phosphoramidate monoester, cyclic phosphoramidate, cyclic phosphorodiamidate, phosphoramidate diester, and —C(O)CHR³NH₂, where R³ is a sidechain of an amino acid, or where W and W¹ may optionally join together to form a cyclic phosphonamidate; and or pharmaceutically acceptable salts or partial salts thereof, wherein substituted alkyl refers to an alkyl group having from 1 to 3 substituents selected from the group consisting of alkoxy, substituted alkoxy, acyl, acylamino, acyloxy, oxyacyl, amino, substituted amino, alninoacyl, aryl, substituted aryl, aryloxy, substituted aryloxy, cyano halogen, hydroxyl, nitro, carboxyl, carboxyl esters, cycloalkyl, substituted cycloalkyl, heteroaryl, substituted heteroaryl, heterocyclyl, and substituted heterocyclyl;

alkoxy refers to alkyl-O—;

substituted alkoxy refers to (substituted alkyl)-O—;

acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclyl-C(O)—, and substituted heterocyclyl-C(O)—;

acylamino refers to —C(O)NR⁴R⁴ where each R⁴ independently is selected from the group consisting of hydrogen, alkyl, substituted alkyl; alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R⁴ is joined to form together with the nitrogen atom a heterocyclyl or substituted heterocyclyl ring;

acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclyl-C(O)O—, and substituted heterocyclyl-C(O)O—;

oxyacyl refers to a moiety selected from the group consisting of alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl—OC(O)—, heteroaryl-OC(O)—, substituted heteroaryl-OC(O)—, heterocyclyl-OC(O)—, and substituted heterocyclyl-OC(O)—;

substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proviso that any hydroxyl substitution is not attached to an unsaturated carbon atom;

substituted alkynyl refers ro an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl amino refers to —NH₂;

substituted amino refers to —NR'R" where R' and R" independently are selected from the group consisting of hydrogen, alkyl, substituted alkyl, alkenyl, substituted alkeynyl, alkynyl, substituted alkynyl, aryl, substituted aryl, cycloalkyl, substituted cycloalkyl, heteroaryl substituted heteroaryl, heterocyclyl, substituted heterocyclyl and where R' and R" are joined, together with the nitrogen bound thereto to form a heterocyclyl or substituted heterocyclyl ring provided that R' and R" are both not hydrogen;

aminoacyl refers to a moiety selected from the group consisting of —NR⁵C(O)alkyl, —NR⁵C(O)substituted alkyl, —NR⁵C(O)cycloalkyl, —NR⁵C(O)substituted cycloalkyl, —NR⁵C(O)alkenyl, —NR⁵C(O)substituted alkenyl, —NR⁵C(O)alkynyl, —NR⁵C(O)substituted alkynyl, —NR⁵C(O)aryl, —NR⁵C(O)substituted aryl, —NR⁵C(O)heteroaryl, —NR⁵C(O)substituted heteroaryl, —NR⁵C(O)heterocyclyl, and —NR⁵C(O) substituted heterocyclyl where R⁵ is hydrogen or alkyl;

aryl refers to a monoyalent aromatic carbocyclic group of from 6 to 14 carbon atoms having a single ring or multiple condensed rings which condensed rings may or may not be aromatic provided that the point of attachment is at an aromatic carbon atom;

substituted aryl refers to an aryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

aryloxy refers to aryl-O—;

substituted aryloxy refers to (substituted aryl)-O—;

carboxyl refers to —OOOH or salts thereof;

carboxyl ester refers to a moiety selected from the group consisting of —C(O)O-alkyl, —C(O)O—substituted alkyl, -C(O)Oaryl, and —C(O)O-substituted aryl;

cycloalkyl refers to a cyclic alkyl group of from 3 to 10 carbon atoms having single or multiple cyclic rings;

substituted cycloalkyl refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

cycloalkoxy refers to —O-cycloalkyl;

substituted cycloalkoxy refers to —O-(substituted cycloalkyl);

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur, —S(O)— and —SO$_2$,— within the ring, wherein the heteroaryl group can have a single ring or multiple condensed rings wherein the condensed rings may or may not be aromatic and/or contain a heteroatom provided that the point of attachment is through an aromatic ring atom;

substituted heteroaryl refers to a heteroaryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated group having a single ring or multiple condensed rings, from 1 to 10 carbon atoms and from 1to 4 hetero atoms selected from the group consisting of nitrogen, oxygen, sulfur, —S(O)—, and —S(O)$_2$— within the ring wherein, in fused ring systems, one or more the rings can be cycloalkyl, aryl or heteroaryl provided that the point of attachment is through the heterocyclyl ring;

substituted heterocyclyl refers to a heterocyclyl group substituted with from 1 to 3 substituents selected from the group consisting of oxo (═O), thioxo (═S), alkyl, substituted alkyl, alkoxy, substituted alkoxy, acyl, acylamino, acyloxy, amino, substituted amino, aminoacyl, aryl, substituted aryl, acyloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl substituted heterocyclyloxy refers to —O-(substituted heterocyclyl;

phosphate refers to a moiety selected from the group consisting of —OP(O)(OH)$_2$ (monophosphate or phospho), —OP(O)(OH)OP(O)(OH)$_2$(triphosphate or tridiphospho) and —OP(O)(OH)OP(O)(OH)OP(O)(OH)$_2$ (triphosphate or triphospho) and salts thereof, including partial salts thereof;

phosphate ester refers to a mono-, di- and tri-phosphate-group, wherein one or more of the hydroxyl groups is replaced by an alkoxy group;

phosphonate refers to a moiety selected from the group consisting of —OP(O)(R$^6$)(OH) and —OP(O)(R$^6$)(OR$^6$) and salts thereof, including partial salts thereof, wherein each R$^6$ is independently selected from hydrogen, alkyl, substituted alkyl, carboxyl, and carboxyl ester;

phosphorodiamidate refers to

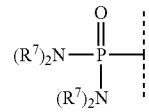

where each R$^7$ may be the same or different and each is hydrogen, alkyl, substituted alkyl, cycloalkyl, or substituted cycloalkyl;

phosphoramidate monoester refers to

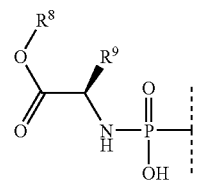

where R$^8$ is hydrogen or alkyl and R$^9$ maybe the same or different and each is hydrogen, alkyl, substituted alkyl, cycloalkyl, or substituted cycloalkyl;

phosphoramidate diester refers to

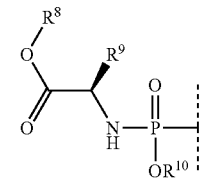

where R$^8$ is hydrogen or alkyl, R$^{10}$ is aryl, substituted aryl, alkyl, or substutituted alkyl, and each R$^9$ is hydrogen, alkyl, substituted alkyl, cycloalkyl, and substituted cycloalkyl;

cyclic phosphoramidate refers to

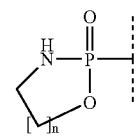

where n is 1 to 3;

cyclic phosphorodiamidate refers to

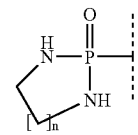

where n is 1 to 3;

phosphonamide refers to

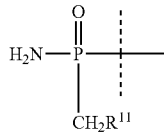

where $R^{11}$ is hydrogen, alkyl, substituted alkyl, cycloalkyl, or substituted cycloalkyl;
thiol refers to —SH;
thioalkyl refers to —S-alkyl;
substituted thioalkyl refers to —S-(substituted alkyl);
thiocycloalkyl refers to —S-cycloalkyl;
substituted thiocycloalkyl refers to —S-(substituted cycloalkyl);
thioaryl refers to —S-aryl;
substituted thioaryl refers to —S-(substituted aryl);
thioheteroaryl refers to —S-heteroaryl;
substituted thioheteroaryl refers to —S-(substituted heteroaryl);
thioheterocyclyl refers to —S-heterocyclyl; and
substituted thioheterocyclyl refers to —S-(substituted heterocyclyl).

6. A compound selected from the group consisting of:
7-(2'-C-methyl-β-D-ribofuranosyl)-4-amino-5-(2-carboxyethyn-1-yl)-pyrrolo[2,3-d]pyrimidine;
7-(2'-C-methyl-5'-phospho-β-D-ribofuranosyl)-4-amino-5-(2-carboxyethyn-1-yl)-pyrrolo[2,3-d]pyrimidine;
7-(2'-C-methyl-5'-diphospho-β-D-ribofuranosyl)-4-amino-5-(2-carboxyethyn-1-yl)-pyrrolo[2,3-d]pyrimidine; and
7-(2'-C-methyl-5'-triphospho-β-D-ribofuranosyl)-4-amino-5-(2-carboxyethyn-1-yl)-pyrrolo[2,3-d]pyrimidine;
or pharmaceutically acceptable salts or partial salts thereof.

7. A pharmaceutical composition comprising a pharmaceutically acceptable diluent and a therapeutically effective amount of a compound according to any one of claims 5 and 6.

8. method for treating hepatitis C virus (HCV) in a mammalian patient suffering from HCV which method comprises administering to said mammal a pharmaceutical composition according to claim 7.

9. A compound of formula III:

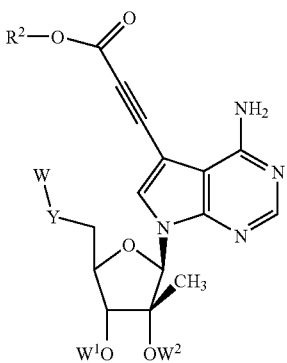

wherein
Y is selected from the group consisting of a bond, —CH$_2$— or —O—;
$R^2$ is alkyl;
each of W, $W^1$ and $W^2$ is independently selected from the group consisting of hydrogen, acyl, oxyacyl, phosphonate, phosphate esters, phosphate, phospho, diphospho, triphospho, phosphonamidate, phosphorodiamidate, phosphoramidate monoester, cyclic phosphoramidate, cyclic phosphorodiamidate, phosphoramidate diester, and —C(O)CHR$^3$NH$_2$, where R$^3$ is a sidechain of an amino acid, or where W and $W^1$ may optionally join together to form a cyclic phosphonamidate; and
or pharmaceutically acceptable salts or partial salts thereof, wherein
substituted alkyl refers to an alkyl group having from 1 to 3 substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
alkoxy refers to alkyl-O—;
substituted alkoxy refers to (substituted alkyl)-O—;
acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclyl-C(O)—, and substituted heterocyclyl-C(O)—;
acylamino refers to —C(O)NR$^4$R$^4$ where each R$^4$ independently is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R$^4$ is joined to form together with the nitrogen atom a heterocyclyl or substituted heterocyclyl ring;
acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl—C(O)O—, heteroaryl-C(O)O—, substituted heteroaryl-C(O)O—, heterocyclyl-C(O)O—, and substituted heterocyclyl-C(O)O—;
oxyacyl refers to a moiety selected from the group consisting of alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclyl-OC(O)—, and substituted heterocyclyl-OC(O)—;
substituted alkenyl refers to an alkenyl group having from 1 to 3 substituents selected from the group consisting of alko y, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proyiso that any hydroxyl substitution is not attached to an unsaturated carbon atom;

substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl amino refers to —$NH_2$;

substituted amino refers to —NR'R" where R' and R" independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where R' and R" are joined, together with the nitrogen bound thereto to form a heterocyclyl or substituted heterocyclyl ring provided that R' and R" are both not hydrogen;

aminoacyl refers to a moiety selected from the group consisting of —$NR^5C(O)$alkyl, —$NR^5C(O)$substituted alkyl, —$NR^5C(O)$cycloalkyl, —$NR^5C(O)$substituted cycloalkyl, —$NR^5C(O)$alkenyl, —$NR^5C(O)$substituted alkenyl, —$NR^5C(O)$alkynyl, —$NR^5C(O)$substituted alkynyl, —$NR^5C(O)$aryl, —$NR^5C(O)$substituted aryl, —$NR^5C(O)$heteroaryl, —$NR^5C(O)$substituted heteroaryl, —$NR^5C(O)$heterocyclyl, and —$NR^5C(O)$ substituted heterocyclyl where $R^5$ is hydrogen or alkyl;

aryl refers to a monovalent aromatic carbocyclic group of from 6 to 14 carbon atoms having a single ring or multiple condensed rings which condensed rings may or may not be aromatic provided that the point of attachment is at an aromatic carbon atom;

substituted aryl refers to an aryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

aryloxy refers to aryl-O—;

substituted aryloxy refers to (substituted aryl)-O—;

carboxyl refers to —COOH or salts thereof;

carboxyl ester refers to a moiety selected from the group consisting of —C(O)O-alkyl, —C(O)O- substituted alkyl, —C(O)Oaryl, and —C(O)O-substituted aryl;

cycloalkyl refers to a cyclic alkyl group of from 3 to 10 carbon atoms having single or multiple cyclic rings;

substituted cycloalkyl refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

cycloalkoxy refers to —O-cycloalkyl;

substituted cycloalkoxy refers to —O-(substituted cycloalkyl);

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur, —S(O)— and —$SO_2$— within the ring, wherein the heteroaryl group can have a single ring or multiple condensed rings wherein the condensed rings may or may not be aromatic and/or contain a heteroatom provided that the point of attachment is through an aromatic ring atom;

substituted heteroaryl refers to a heteroaryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated group having a single ring or multiple condensed rings, from 1 to 10 carbon atoms and from 1 to 4 hetero atoms selected from the group consisting of nitrogen, oxygen, sulfur, —S(O)—, and —$S(O)_2$— within the ring wherein, in fused ring systems, one or more the rings can be cycloalkyl, aryl or heteroaryl provided that the point of attachment is through the heterocyclyl ring;

substituted heterocyclyl refers to a heterocyclyl group substituted with from 1 to 3 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl substituted heterocyclyloxy refers to —O-(substituted heterocyclyl);

phosphate refers to a moiety selected from the group consisting of —$OP(O)(OH)_2$ (monophosphate or phospho), —$OP(O)(OH)OP(O)(OH)_2$ (diphosphate or diphospho) and —$OP(O)(OH)OP(O)(OH)OP(O)(OH)_2$ (triphosphate or triphospho) and salts thereof, including partial salts thereof;

phosphate ester refers to a mono-, di- and tri-phosphate group, wherein one or more of the hydroxyl groups is replaced by an alkoxy group;

phosphonate refers to a moiety selected from the group consisting of —$OP(O)(R^6)(OH)$ and —$OP(O)(R^6)(OR^6)$ and salts thereof, including partial salts thereof, wherein each $R^6$ is independently selected from hydrogen, alkyl, substituted alkyl, carboxyl, and carboxyl ester;

phosphorodiamidate refers to

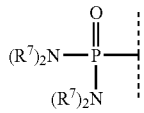

where each $R^7$ may be the same or different and each is hydrogen, alkyl, substituted alkyl, cycloalkyl, or substituted cycloalkyl;

phosphoramidate monoester refers to

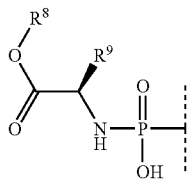

where $R^8$ is hydrogen or alkyl and $R^9$ may be the same or different and each is hydrogen, alkyl, substituted alkyl, cycloalkyl, or substituted cycloalkyl;

phosphoramidate diester refers to

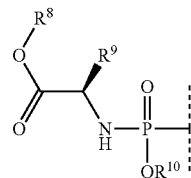

where $R^8$ is hydrogen or alkyl, $R^{10}$ is aryl, substituted aryl, alkyl, or substutituted alkyl, and each $R^9$ is hydrogen, alkyl, substituted alkyl, cycloalkyl, and substituted cycloalkyl;

cyclic phosphoramidate refers to

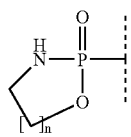

where n is 1 to 3;

cyclic phosphorodiamidate refers to

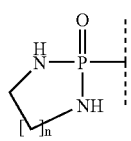

where n is 1 to 3;

phosphonamidate refers to

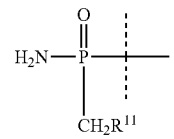

where $R^{11}$ is hydrogen, alkyl, substituted alkyl, cycloalkyl, or substituted cycloalkyl;

thiol refers to —SH;
thioalkyl refers to —S-alkyl;
substituted thioalkyl refers to —S-(substituted alkyl);
thiocycloalkyl refers to —S-cycloalkyl;
substituted thiocycloalkyl refers to —S-(substituted cycloalkyl);
thioaryl refers to —S-aryl;
substituted thioaryl refers to —S-(substituted aryl);
thioheteroaryl refers to —S-heteroaryl;
substituted thioheteroaryl refers to —S-(substituted heteroaryl);
thioheterocyclyl refers to —S-heterocyclyl; and
substituted thioheterocyclyl refers to —S-(substituted heterocyclyl).

10. A compound selected from the group consisting of:
7-(2'-C-methyl-β-D-ribofuranosyl)-4-amino-5-[(ethyl 2-carboxyl)ethyn-1-yl]-pyrrolo[2,3-d]pyrimidine;
7-(2'-C-methyl-β-D-ribofuranosyl)-4-amino-5-[(methyl 2-carboxyl)ethyn-1-yl]-pyrrolo[2,3-d]pyrimidine;
7-(2'-C-methyl-5'-phospho-β-D-ribofuranosyl)-4-amino-5-[(ethyl 2-carboxyl)ethyn-1-yl]-pyrrolo[2,3-d]pyrimidine;
7-(2'-C-methyl-5'-phospho-β-D-ribofuranosyl)-4-amino-5-[(methyl 2-carboxyl)ethyn-1-yl]-pyrrolo[2,3-d]pyrimidine;
7-(2'-C-methyl-5'-diphospho-β-D-ribofuranosyl)-4-amino-5-[(ethyl 2-carboxyl)ethyn-1-yl]-pyrrolo[2,3-d]pyrimidine;
7-(2'-C-methyl-5'-diphospho-β-D-ribofuranosyl)-4-amino-5-[(methyl 2-carboxyl)ethyn-1-yl]-pyrrolo[2,3-d]pyrimidine;
7-(2'-C-methyl-5'-triphospho-β-D-ribofuranosyl)-4-amino-5-[(ethyl 2-carboxyl)ethyn-1-yl]-pyrrolo[2,3-d]pyrimidine; and
7-(2'-C-methyl-5'-triphospho-β-D-ribofuranosyl)-4-amino-5-[(methyl 2-carboxyl)ethyn-1-yl]-pyrrolo[2,3-d]pyrimidine;

or pharmaceutically acceptable salts or partial salts thereof.

11. A pharmaceutical composition comprising a pharmaceutically acceptable diluent and a therapeutically effective amount of a compound according to any one of claims 9 and 10.

12. A method for treating hepatitis C virus (HCV) in a mammalian patient suffering from HCV which method comprises administering to said mammal a pharmaceutical composition according to claim 11.

13. A compound of formula V:

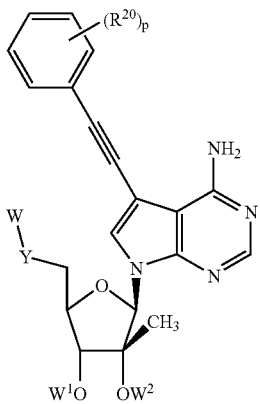

V wherein
Y is selected from the group consisting of a bond, —CH₂— or —O—;
each of W, W¹ and W² is independently selected from the group consisting of hydrogen, acyl, oxyacyl, phosphonate, phosphate esters, phosphate, phospho, diphospho, tiphospho, phosphonamidate, phosphorodiamidate, phosphoramidate monoester, cyclic phosphoramidate, cyclic phosphorodimidate, phosphoramidate diester, and —C(O) CHR³NH₂, where R³ is a sidechain of an amino acid, or where W and W¹ may optionally join together to form a cyclic phosphonamidate;
R²⁰ is selected from the group consisting of hydrogen, carboxyl, carboxyl esters, phenyl, and phenyl substituted with from 1 to 2 substitutents selected from the group consisting of methyl, ethyl, and halo; and
p is 0, 1, or 2;
or pharmaceutically acceptable salts or partial salts thereof, wherein
substituted alkyl refers to an alkyl group having from 1 to 3 substituents selected from the group consisting of alkoxy, substituted alkoxy, acyl, acylamino, acyloxy, oxyacyl, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;
alkoxy refers to alkyl-O—;
substituted alkoxy refers to (substituted alkyl)-O—;
acyl refers to a moiety selected from the group consisting of H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclyl-C(O)—, and substituted heterocyclyl-C(O)—;
acylamino refers to —C(O)NR⁴R⁴ independently is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where each R⁴ is joined to form together with the nitrogen atom a heterocyclyl or substituted heterocyclyl ring;
acyloxy refers to a moiety selected from the group consisting of alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclyl-C(O)O—, and substituted heterocyclyl-C(O)O—;
oxyacyl refers to a moiety selected from the group consisting of alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclyl-OC(O)—, and substituted heterocyclyl-OC(O)—;
substituted alkenyl refers to an alkenyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl with the proviso that any hydroxyl substitution is not attached to an unsaturated carbon atom;
substituted alkynyl refers to an alkynyl group having from 1 to 3 substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroarayl, substituted heteroaryl, heterocyclyl, and substituted heterocyclyl
amino refers to —NH₂;
substituted amino refers to —NR'R" where R' and R" independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclyl, substituted heterocyclyl and where R' and R" are joined, together with the nitrogen bound thereto to form a heterocyclyl or substituted heterocyclyl ring provided that R' and R" are both not hydrogen;
aminoacyl refers to a moiety selected from the group consisting of —NR⁵C(O)alkyl, —NR⁵C(O)substituted alkyl, —NR⁵C(O)cycloalkyl, —NR⁵C(O)substituted cycloalkyl, —NR⁵C(O)alkenyl, —NR⁵C(O)substituted alkenyl, —NR⁵C(O)alkynyl, —NR⁵C(O)substituted alkynyl, —NR⁵C(O)aryl, —NR⁵C(O)substituted aryl, —NR⁵C(O)heteroaryl, —NR⁵C(O)substituted heteroaryl, —NR⁵C(O)heterocyclyl, and —NR⁵C(O) substituted heterocyclyl where R⁵ is hydrogen or alkyl;
aryl refers to a monoyalent aromatic carbocyclic group of from 6 to 14 carbon atoms having a single ring or multiple condensed rings which condensed rings may or may not be aromatic provided that the point of attachment is at an aromatic carbon atom;
substituted aryl refers to an aryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted) aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

aryloxy refers to aryl-O—;

substituted aryloxy refers to (substituted aryl)-O—;

carboxyl refers to —COOH or salts thereof;

carboxyl ester refers to a moiety selected from the group consisting of —C(O)O-alkyl, —C(O)O- substituted alkyl, —C(O)Oaryl, and —C(O)O-substituted aryl;

cycloalkyl refers to a cyclic alkyl group of from 3 to 10 carbon atoms having single or multiple cyclic rings;

substituted cycloalkyl refers to a cycloalkyl having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

cycloalkoxy refers to —O-cycloalkyl;

substituted cycloalkoxy refers to —O-(substituted cycloalkyl);

halogen refers to fluoro, chloro, bromo or iodo;

heteroaryl refers to an aromatic group of from 1 to 10 carbon atoms and 1 to 4 heteroatoms selected from the group consisting of oxygen, nitrogen, sulfur, —S(O)— and —SO$_2$— within the ring, wherein the heteroaryl group can have a single ring or multiple condensed rings wherein the condensed rings may or may not be aromatic and/or contain a heteroatom provided that the point of attachment is through an aromatic ring atom;

substituted heteroaryl refers to a heteroaryl group substituted with from 1 to 3 substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, cycloalkoxy, substituted cycloalkoxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclyl, substituted thioheterocyclyl, cycloalkyl, substituted cycloalkyl, halo, nitro, heteroaryl, substituted heteroaryl, heterocyclyl, substituted heterocyclyl, heteroaryloxy, substituted heteroaryloxy, heterocyclyloxy, and substituted heterocyclyloxy;

heteroaryloxy refers to —O-heteroaryl;

substituted heteroaryloxy refers to —O-(substituted heteroaryl);

heterocyclyl refers to a saturated or unsaturated group having a single ring or multiple condensed rings, from 1 to 10 carbon atoms and from 1 to 4 hetero atoms selected from the group consisting of nitrogen, oxygen, sulfur, —S(O)—, and —S(O)$_2$— within the ring wherein, in fused ring systems, one or more the rings can be cycloalkyl, aryl or heteroaryl provided that the point of attachment is through the heterocyclyl ring;

substituted heterocyclyl refers to a heterocyclyl group substituted with from 1 to 3 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclyl, and substituted heterocyclyl;

heterocyclyloxy refers to —O-heterocyclyl substituted heterocyclyloxy refers to —O-(substituted heterocyclyl);

phosphate refers to a moiety selected from the group consisting of —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) and salts thereof, including partial salts thereof;

phosphate ester refers to a mono-, di- and tri-phosphate group, wherein one or more of the hydroxyl groups is replaced by an alkoxy group;

phosphonate refers to a moiety selected from the group consisting of —OP(O)(R$^6$)(OH) and —OP(O)(R$^6$)(OR$^6$) and salts thereof, including partial salts thereof, wherein each R$^6$ is independently selected from hydrogen, alkyl substituted alkyl, carboxyl, and carboxyl ester;

phosphorodiamidate refers to

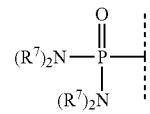

where each R$^7$ may be the same or different and each is hydrogen, alkyl, substituted alkyl, cycloalkyl, or substituted cycloalkyl;

phosphoramidate monoester refers to

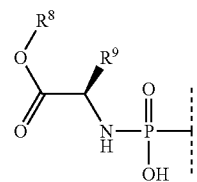

where R$^8$ is hydrogen or alkyl and R$^9$ may be the same or different and each is hydrogen, alkyl, substituted alkyl, cycloalkyl, or substituted cycloalkyl;

phosphoramidate diester refers to

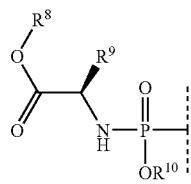

where $R^8$ is hydrogen or alkyl, $R^{10}$ is aryl, substituted aryl, alkyl, or substututed alkyl, and each $R^9$ is hydrogen, alkyl, substituted alkyl, cycloalkyl, and substituted cycloalkyl;
cyclic phosphoramidate refers to

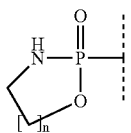

where n is 1 to 3;
cyclic phosphorodiamidate refers to

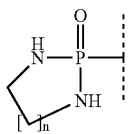

where n is 1 to 3;
phosphonamidate refers to

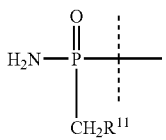

where $R^{11}$ is hydrogen, alkyl, substituted alkyl, cycloalkyl, or substituted cycloalkyl;
thiol refers to —SH;
thioalkyl refers to —S-alkyl;
substituted thioalkyl refers to —S-(substituted alkyl);
thiocycloalkyl refers to —S-cycloalkyl;
substituted thiocycloalkyl refers to —S-(substituted cycloalkyl);
thioaryl refers to —S-aryl;
substituted thioaryl refers to —S-(substituted aryl);
thioheteroaryl refers to —S-heteroaryl;
substituted thioheteroaryl refers to —S-(substituted heteroaryl);
thioheterocyclyl refers to —S-heterocyclyl; and
substituted thioheterocyclyl refers to —S-(substituted heterocyclyl).
14. A compound selected from the group consisting of:
7-(2'-C-methyl-β-D-ribofuranosyl)-4-amino-5-(2-phenylethyn-1-yl)-pyrrolo[2,3-d]pyrimidine;
7-(2'-C-methyl-β-D-ribofuranosyl)-4-amino-5-(2-(4-fluorophenyl)ethyn-1-yl)-pyrrolo[2,3-d]pyrimidine;
7-(2'-C-methyl-β-D-ribofuranosyl)-4-amino-5-(2-(4-methylphenyl)ethyn-1-yl)-pyrrolo[2,3-d]pyrimidine;
7-(2'-C-methyl-5'-phospho-β-D-ribofuranosyl)-4-amino-5-(2-phenylethyn-1-yl)-pyrrolo[2,3-d]pyrimidine;
7-(2'-C-methyl-5'-phospho-β-D-ribofuranosyl)-4-amino-5-(2-(4-fluorophenyl)ethyn-1-yl)-pyrrolo[2,3-d]pyrimidine;
7-(2'-C-methyl-5'-phospho-β-D-ribofuranosyl)-4-amino-5-(2-(4-methylphenyl)ethyn-1-yl)-pyrrolo[2,3-d]pyrimidine;
7-(2'-C-methyl-5'-diphospho-β-D-ribofuranosyl)-4-amino-5-(2-phenylethyn-1-yl)-pyrrolo[2,3-d]pyrimidine;
7-(2'-C-methyl-5'-diphospho-β-D-ribofuranosyl)-4-amino-5-(2-(4-fluorophenyl)ethyn-1-yl)-pyrrolo[2,3-d]pyrimidine;
7-(2'-C-methyl-5'-diphosphol-β-D-ribofuranosyl)-4-amino-5-(2-(4-methylphenyl)ethyn-1-yl)-pyrrolo[2,3-d]pyrimidine;
7-(2'-C-methyl-5'-triphosphol-β-D-ribofaranosyl)-4-amino-5-(2-phenylethyn-1-yl)-pyrrolo[2,3-d]pyrimidine;
7-(2'-C-methyl-5'-triphosphol-β-D-ribofuranosyl)-4-amino-5-(2-(4-fluorophenyl)ethyn-1-yl)-pyrrolo[2,3-d]pyrimidine; and
7-(2'-C-methyl-5'-triphosphol-β-D-ribofuranosyl)-4-amino-5-(2-(4-methylphenyl)ethyn-1-yl)-pyrrolo[2,3-d]pyrimidine;
or pharmaceutically acceptable salts or partial salts thereof.

15. A pharmaceutical composition comprising a pharmaceutically acceptable diluent and a therapeutically effective amount of a compound according to any one of claims 13 and 14.

16. A method for treating hepatitis C virus (HCV) in a mammalian patient suffering from HCV which method comprises administering to said mammal a pharmaceutical composition according to claim 15.

17. 7-(2'-C-methyl-β-D-ribofuranosyl)-4-amino-5-(ethen-1-yl)-pyrrolo[2,3-d]pyrimidine or a pharmaceutically acceptable salt or partial salt thereof.

18. 7-(2'-C-methyl-β-D-ribofuranosyl)-4-amino-5-(2-cis-methoxy-ethen-1-yl)-pyrrolo[2,3-d]pyrimidine or a pharmaceutically acceptable salt or partial salt thereof.

19. 7-(2'-C-methyl-β-D-ribofuranosyl)-4-amino-5-(2-phenylethyn-1-yl)-pyrrolo[2,3-d]pyrimidine or a pharmaceutically acceptable salt or partial salt thereof.

20. 7-(2'-C-methyl-β-D-ribofuranosyl)-4-amino-5-(2-(4-fluorophenyl)ethyn-1-yl)-pyrrolo[2,3-d]pyrimidine or a pharmaceutically acceptable salt or partial salt thereof.

21. 7-(2'-C-methyl-β-D-ribofuranosyl)-4-amino-5-(2-(4-methylphenyl)ethyn-1-yl)-pyrrolo[2,3-d]pyrimidine or a pharmaceutically acceptable salt or partial salt thereof.

22. 7-(2'-C-methyl-β-D-ribofuranosyl)-4-amino-5-(2-carboxyethyn-1-yl)-pyrrolo[2,3-d]pyrimidine or a pharmaceutically acceptable salt or partial salt thereof.

23. 7-(2'-C-methyl-β-D-ribofuranosyl)-4-amino-5-[(ethyl 2-carboxyl)ethyn-1-yl]-pyrrolo[2,3-d]pyrimidine or a pharmaceutically acceptable salt or partial salt thereof.

24. 7-(2'-C-methyl-β-D-ribofuranosyl)-4-amino-5-[(methyl 2-carboxyl)ethyn-1-yl]-pyrrolo[2,3-d]pyrimidine or a pharmaceutically acceptable salt or partial salt thereof.

* * * * *

UNITED STATES PATENT AND TRADEMARK OFFICE
CERTIFICATE OF CORRECTION

PATENT NO. : 7,202,223 B2
APPLICATION NO. : 10/861090
DATED : April 10, 2007
INVENTOR(S) : Christopher D. Roberts and Jesse D. Keicher It is certified that error appears in the above-identified patent and that said Letters Patent is hereby corrected as shown below:

In Claim 1, at column 61, line 41, please replace "$CHR^3\ NH_2$" with -- $CHR^3NH_2$ --

In Claim 1, at column 61, line 49, please replace "alkenyl group" with -- alkyl group --

In Claim 1, at column 61, line 52, please replace "anryl," with -- aryl, --

In Claim 1, at column 61, line 61, please replace "-H-C(O)-,alkyl-C(O)-," with -- H-C(O)-, alkyl-C(O)-, --

In Claim 1, at column 61, line 62, please replace "alkenyl-C(O)-, substituted alkynyl-C(O)-," with -- alkenyl-C(O)-, substituted alkenyl-C(O)-, --

In Claim 1, at column 61, line 66, please replace "hetercylyclyl-C(O)-," with -- heterocyclyl-C(O)-, --

In Claim 1, at column 62, line 32, please replace "substituted heteroaryl-C(O)-heterocyclyl-C(O)-" with -- substituted heteroaryl-C(O)-, heterocyclyl-C(O)- --

In Claim 1, at column 62, line 47, please replace "substituted and, aryloxy" with -- substituted aryl, aryloxy --

In Claim 1, at column 62, line 66, please replace "heteroayl" with -- heteroaryl --

In Claim 1, at column 63, line 12, please replace "-$NR^5$C(C)heterocyclyl," with -- -$NR^5$C(O)heterocyclyl, --

In Claim 3, at column 66, line 34-35, please replace "claims 1 to and 2" with -- claims 1 and 2 --

UNITED STATES PATENT AND TRADEMARK OFFICE
CERTIFICATE OF CORRECTION

PATENT NO.       : 7,202,223 B2
APPLICATION NO.  : 10/861090
DATED            : April 10, 2007
INVENTOR(S)      : Christopher D. Roberts and Jesse D. Keicher It is certified that error appears in the above-identified patent and that said Letters Patent is hereby corrected as shown below:

In Claim 5, at column 67, line 9, please replace "alninoacyl," with -- aminoacyl, --

In Claim 5, at column 67, line 29, please replace "alkynyl, substituted alkenyl," with -- alkynyl, substituted alkynyl, --

In Claim 5, at column 67, line 62, please replace "refers ro" with -- refers to --

In Claim 5, at column 68, line 7, please replace "substituted alkeynyl," with -- substituted alkenyl, --

In Claim 5, at column 68, line 23, please replace "monoyalent" with -- monovalent --

In Claim 5, at column 68, line 47, please replace "refers to -OOOH" with -- refers to -COOH --

In Claim 5, at column 69, line 3, please replace "haye" with -- have --

In Claim 5, at column 69, line 43, please replace "acyloxy," with -- aryloxy, --

In Claim 5, at column 69, line 54-55, please replace "-OP(O)(OH)OP(O)(OH)$_2$ (triphospate or triphospho)" with -- -OP(O)(OH)OP(O)(OH)$_2$ (diphosphate or diphospho) --

In Claim 9, at column 72, line 60, please replace "alko y," with -- alkoxy, --

In Claim 9, at column 72, line 66, please replace "proyiso" with -- proviso --

In Claim 9, at column 74, line 9, please replace "haye" with -- have --

In Claim 13, at column 77, line 28, please replace "tiphospho," with -- triphospho, --

UNITED STATES PATENT AND TRADEMARK OFFICE
CERTIFICATE OF CORRECTION

PATENT NO. : 7,202,223 B2
APPLICATION NO. : 10/861090
DATED : April 10, 2007
INVENTOR(S) : Christopher D. Roberts and Jesse D. Keicher It is certified that error appears in the above-identified patent and that said Letters Patent is hereby corrected as shown below:

In Claim 13, at column 77, line 30, please replace "cyclic phosphorodimidate" with -- cyclic phosphorodiamidate --

In Claim 13, at column 77, line 37, please replace "substitutents" with -- substituents --

In Claim 13, at column 78, line 28, please replace "proyiso" with -- proviso --

In Claim 13, at column 78, line 36, please replace "heteroarayl," with -- heteroaryl, --

In Claim 13, at column 78, line 58, please replace "Monoyalent" with -- monovalent --

In Claim 13, at column 79, line 1, please replace "substituted) aryl," with -- substituted aryl, --

In Claim 13, at column 79, line 5, please replace "thiaaryl," with -- thioaryl, --

In Claim 13, at column 79, line 38, please replace "haye" with -- have --

In Claim 14, at column 82, line 21, please replace "ribofaranosyl" with -- ribofuranosyl --

Signed and Sealed this

Tenth Day of June, 2008

JON W. DUDAS
*Director of the United States Patent and Trademark Office*

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aggacatgga tccgcggggt cgggcacgag acag          34

```
<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggctggca tgcactcaat gtcctacaca tggac                                35
```